US010449220B2

(12) United States Patent
Koob

(10) Patent No.: US 10,449,220 B2
(45) Date of Patent: Oct. 22, 2019

(54) MICRONIZED PLACENTAL COMPOSITIONS COMPRISING A CHELATOR

(71) Applicant: MiMedx Group, Inc., Marietta, GA (US)

(72) Inventor: Thomas J. Koob, Marietta, GA (US)

(73) Assignee: MiMedx Group, Inc., Marietta, GA (US)

(*) Notice: Subject to any disclaimer, the term of this patent is extended or adjusted under 35 U.S.C. 154(b) by 199 days.

(21) Appl. No.: 14/472,150

(22) Filed: Aug. 28, 2014

(65) Prior Publication Data

US 2015/0064274 A1 Mar. 5, 2015

Related U.S. Application Data

(60) Provisional application No. 61/872,393, filed on Aug. 30, 2013.

(51) Int. Cl.
A61K 35/50 (2015.01)
A61K 33/24 (2019.01)
A61K 45/06 (2006.01)
A61K 47/54 (2017.01)

(52) U.S. Cl.
CPC .............. A61K 35/50 (2013.01); A61K 33/24 (2013.01); A61K 45/06 (2013.01); A61K 47/547 (2017.08)

(58) Field of Classification Search
None
See application file for complete search history.

(56) References Cited

U.S. PATENT DOCUMENTS

| 4,703,108 A | 10/1987 | Silver et al. |
| 4,847,049 A | 7/1989 | Yamamoto |
| 5,541,232 A | 7/1996 | Howell et al. |
| 5,807,581 A | 9/1998 | Rosenblatt et al. |
| 6,129,757 A | 10/2000 | Weadock |
| 6,166,184 A | 12/2000 | Hendriks et al. |
| 6,565,960 B2 | 5/2003 | Koob et al. |
| 6,682,760 B2 | 1/2004 | Noff et al. |
| 6,716,895 B1 | 4/2004 | Terry |
| 6,821,530 B2 | 11/2004 | Koob et al. |
| 7,101,857 B2 | 9/2006 | Sung et al. |
| 8,071,135 B2 | 12/2011 | Liu et al. |
| 8,105,634 B2 | 1/2012 | Liu et al. |
| 8,192,481 B2 | 6/2012 | King |
| 8,323,701 B2 | 12/2012 | Daniel et al. |
| 8,357,403 B2 | 1/2013 | Daniel et al. |
| 8,623,421 B2 | 1/2014 | Daniel |
| 8,858,633 B2 | 10/2014 | Koob et al. |
| 8,946,163 B2 | 2/2015 | Koob |
| 9,155,799 B2 | 10/2015 | Koob |
| 2003/0187515 A1 | 10/2003 | Hariri et al. |
| 2004/0048796 A1 | 3/2004 | Hariri et al. |
| 2005/0142161 A1 | 6/2005 | Freeman et al. |
| 2005/0250171 A1 | 11/2005 | Greenwalt |
| 2007/0020225 A1 | 1/2007 | Abramson et al. |
| 2007/0021762 A1 | 1/2007 | Liu et al. |
| 2007/0160573 A1 | 7/2007 | Gengrinovitch |
| 2007/0248575 A1 | 10/2007 | Connor et al. |
| 2007/0299043 A1 | 12/2007 | Hunter et al. |
| 2008/0161917 A1 | 7/2008 | Koob et al. |
| 2008/0181935 A1 | 7/2008 | Bhatia et al. |
| 2008/0233552 A1 | 9/2008 | Ma et al. |
| 2009/0053290 A1 | 2/2009 | Sand et al. |
| 2009/0092664 A1 | 4/2009 | Mumper et al. |
| 2010/0028849 A1 | 2/2010 | Shelby et al. |
| 2010/0094404 A1 | 4/2010 | Greenhalgh et al. |
| 2010/0209408 A1 | 8/2010 | Livesey et al. |
| 2010/0272782 A1 | 10/2010 | Owens et al. |
| 2010/0291182 A1 | 11/2010 | Palasis et al. |
| 2010/0317677 A1 | 12/2010 | Hassel et al. |
| 2011/0097379 A1 | 4/2011 | Yoo et al. |
| 2011/0206776 A1 | 8/2011 | Tom et al. |
| 2012/0010708 A1 | 1/2012 | Young et al. |
| 2012/0135045 A1 | 5/2012 | Nixon et al. |
| 2012/0189571 A1 | 7/2012 | Sengupta et al. |
| 2012/0189583 A1 | 7/2012 | Liu et al. |
| 2012/0189586 A1 | 7/2012 | Harrell |
| 2012/0282348 A1 | 11/2012 | Yates et al. |
| 2013/0344162 A1 | 12/2013 | Morse et al. |
| 2014/0050788 A1 | 2/2014 | Daniel et al. |
| 2014/0052247 A1 | 2/2014 | Daniel et al. |

(Continued)

FOREIGN PATENT DOCUMENTS

DE 289135 A5 4/1991
EP 0 431 479 A1 6/1991

(Continued)

OTHER PUBLICATIONS

Markman et al. Journal of Clinical Oncology, vol. 9, No. 3 Mar. 1991: pp. 389-393.*
Wiley. Processing and Finishing of Polymeric Materials, 2 Volume Set (2011). pp. 403 and 404.*
Houjou et al. J Pharm Pharmacol.;48(5):474-8. (Year: 1996).*
U.S. Appl. No. 13/983,301, filed Aug. 1, 2013, Morse et al.
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
Borkow et al., "Reducing the risk of skin pathologies in diabetics by using copper impregnated socks", Medical Hypotheses, 2009, 1-4, doi:10.1016/j.mehy.2009.02.050.
Hattori et al., "Placental growth factor reconstitutes hematopoiesis by recruiting VEGFR1+ stem cells from bone-marrow microenvironment," Nat. Med., (2002), 8(8):841-849.

(Continued)

Primary Examiner — Amy L Clark
(74) Attorney, Agent, or Firm — Alston & Bird LLP

(57) ABSTRACT

Provided herein are micronized placental compositions composed of micronized placental tissue component, such as amnion or chorion and/or filler bound to one or more chelating agents, which in turn are optionally bound, reversibly, to pharmacologically active metal ions. Further provided are methods of making and using the placental compositions. The compositions have numerous therapeutic applications.

19 Claims, 8 Drawing Sheets

(56) References Cited

U.S. PATENT DOCUMENTS

| | | | |
|---|---|---|---|
| 2014/0052274 | A1 | 2/2014 | Koob et al. |
| 2014/0067058 | A1 | 3/2014 | Koob et al. |
| 2014/0106447 | A1 | 4/2014 | Brown et al. |
| 2014/0205646 | A1 | 7/2014 | Morse et al. |
| 2014/0271728 | A1 | 9/2014 | Koob et al. |
| 2014/0308233 | A1 | 10/2014 | Koob |
| 2014/0342015 | A1 | 11/2014 | Murphy et al. |
| 2014/0356451 | A1 | 12/2014 | Koob |

FOREIGN PATENT DOCUMENTS

| | | | | |
|---|---|---|---|---|
| EP | 0 506 207 | B1 | 11/1999 | |
| FR | 2303529 | A1 * | 10/1976 | ............ A61K 8/982 |
| JP | 04027352 | A * | 1/1992 | |
| JP | 2010/501159 | A | 1/2010 | |
| JP | 2010/540532 | A | 12/2010 | |
| WO | WO-87/00062 | A1 | 1/1987 | |
| WO | WO-88/03805 | A1 | 6/1988 | |
| WO | WO-01/00151 | A1 | 1/2001 | |
| WO | WO-2007/083984 | A1 | 7/2007 | |
| WO | WO-2009/033160 | A1 | 3/2009 | |
| WO | WO-2009/132186 | A1 | 10/2009 | |
| WO | WO-2010/029344 | A2 | 3/2010 | |
| WO | WO-2012/065937 | A1 | 5/2012 | |
| WO | WO-2012/069559 | A1 | 5/2012 | |
| WO | WO-2012/112410 | A2 | 8/2012 | |
| WO | WO-2012/112417 | A2 | 8/2012 | |
| WO | WO-2012/112441 | A1 | 8/2012 | |
| WO | WO-2013/095830 | A1 | 6/2013 | |
| WO | WO-2014/193468 | A1 | 12/2014 | |

OTHER PUBLICATIONS

Kelly et al., "Disparate Effects of Similar Phenolic Phytochemicals as Inhibitors of Oxidative Damage to Cellular DNA", Mutation Res., vol. 485, pp. 309-318, (2001).

Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.

Konishi et al., In vivo anti-tumor effect through the controlled release of cisplatin from biodegradable gelatin hydrogel,: J. Controlled Release, (2003), 92(3):301-313.

Koob et al., "Biological properties of dehydrated human amnion/chorion composite graft: implications for chronic wound healing," International Wound Journal, (2013), 10(5):493-500.

Koob et al., "Mechanical and thermal properties of novel polymerized NDGA-gelatin hydrogels", Biomaterials, Mar. 31, 2003, vol. 24, No. 7, pp. 1285-1292.

Koob et al., Material properties of polymerized NDGA-collagen composite fibers: Development of biologically based tendon constructs. Biomaterials, 23(1): 203-212, 2002.

Kostova, "Platinum Complexes as Anticancer Agents", Recent Patents on Anti-Cancer Drug Discovery, 2006; 1(1):1-22.

Lu et al., "Molecular mechanisms and clinical applications of nordihydroguaiaretic acid (NDGA) and its derivatives: An update," Med. Sci. Monit., (2010), 16(5):RA93-RA100.

MiMedx Group Announces Launch of EpiFixTM and Hiring of Vice President, Wound Care, Mimedx Press Release (2011).

Moussy et al., "Transport characteristics of a novel local drug delivery system using nordihydroguaiaretic acid (NDGA)-polymerized collagen fibers", Biotechnology Progress, Aug. 31, 2007, vol. 23, No. 4, pp. 990-994.

PCT International Preliminary Report of Patentability for PCT Application No. PCT/US14/28975 dated Feb. 6, 2015. 11 pages.

PCT International Preliminary Report on Patentability for International Patent Application No. PCT/US2013/063736 dated Dec. 30, 2014. 21 pages.

PCT International Preliminary Report on Patentability for PCT Patent Application No. PCT/US13/67622. dated Dec. 30, 2014. 8 pages.

PCT International Preliminary Report on Patentability for PCT Patent Application No. PCT/US2013/067618 dated Dec. 3, 2014. 33 pages.

PCT International Preliminary Report on Patentability and Written Opinion for PCT Patent Application No. PCT/US2014/033346 dated Oct. 13, 2015. 8 pages.

PCT International Preliminary Report on Patentability for International Patent Application No. PCT/US2013/054322 dated Dec. 8, 2014. 31 pages.

PCT International Preliminary Report on Patentability for PCT Application No. PCT/US12/24798 dated Feb. 1, 2013. 23 pages.

PCT International Preliminary Report on Patentability for PCT Patent Application No. PCT/US2013/067623. dated Nov. 10, 2014. 16 pages.

PCT International Preliminary Report on Patentability in PCT Patent Application No. PCT/US13/67620 dated Apr. 17, 2015. 16 pages.

PCT International Search Report and Written Opinion for PCT Patent Application No. PCT/US13/67623 dated Apr. 21, 2014. 18 pages.

PCT International Search Report and Written Opinion for PCT Patent Application No. PCT/US2013/055003 dated Nov. 19, 2013. 12 pages.

PCT International Search Report and Written Opinion for PCT Patent Application No. PCT/US2014/028975 dated Jul. 24, 2014. 8 pages.

PCT International Search Report and Written Opinion for PCT Application No. PCT/US12/24798 dated Jun. 20, 2012. 10 pages.

PCT International Search Report and Written Opinion for PCT Patent Application No. PCT/US13/63736 dated Aug. 12, 2014. 11 pages.

PCT International Search Report and Written Opinion for PCT Patent Application No. PCT/US13/67618. dated Apr. 22, 2014. 17 pages.

PCT International Search Report and Written Opinion for PCT Patent Application No. PCT/US13/67620. dated Apr. 22, 2014. 17 pages.

PCT International Search Report and Written Opinion for PCT Patent Application No. PCT/US13/67622 dated Apr. 16, 2014. 17 pages.

PCT International Search Report and Written Opinion for PCT Patent Application No. PCT/US15/12087 dated Apr. 13, 2015. 9 pages.

PCT International Search Report and Written Opinion for PCT Patent Application No. PCT/US2013/054319. dated Nov. 13, 2013. 14 pages.

PCT International Search Report and Written Opinion for PCT Patent Application No. PCT/US2013/054325. dated Oct. 28, 2013. 10 pages.

PCT International Search Report and Written Opinion for PCT Patent Application No. PCT/US2014/033346. dated Aug. 26, 2014. 12 pages.

PCT International Search Report and Written Opinion for PCT Patent Application PCT/US2014/053270 dated Dec. 29, 2014. 14 pages.

PCT International Search Report and Written Opinion in PCT Patent Application No. PTC/US2014/054603 dated Dec. 30, 2014. 12 pages.

Tao, et al., "Implantation of amniotic membrane to reduce postlaminectomy epidural adhesions," Eur. Spine. J., (2009), 18:1202-1212.

Extended European Search Report for European Patent Application No. 14838972.9 dated Apr. 5, 2017.

Office Action for Japanese Application No. 2016-537863 dated Jan. 11, 2019, 5 pages.

Office Action for European Application No. 14838972.9 dated Jan. 31, 2019, 4 pages.

* cited by examiner

MICRONIZED PLACENTAL COMPOSITIONS COMPRISING A CHELATOR

CROSS-REFERENCE TO RELATED APPLICATION

This application claims the benefit under 35 U.S.C. § 119(e) of U.S. Provisional Application No. 61/872,393, filed on Aug. 30, 2013, which is incorporated herein by reference in its entirety.

BACKGROUND OF THE INVENTION

Field of the Invention

This invention is directed to micronized placental compositions comprising micronized placental components and optionally a filler, wherein a biologically compatible chelator moiety is conjugated to a component of the composition. This invention further comprises such compositions having pharmacologically active metal ions reversibly bound to the chelating moiety.

State of the Art

Placental tissue components such as isolated amnion and chorion as well as laminates thereof are known in the art for use as wound coverings and to promote wound healing. Typically, placental tissue is harvested after an elective Cesarean surgery. The placenta is composed of an amniotic membrane which has two primary layers of tissue, amnion and chorion. Amnion tissue is the innermost layer of the amniotic sac and in direct contact with the amniotic fluid. The amniotic sac contains the amniotic fluid and protects the fetal environment. Histological evaluation indicates that the membrane layers of the amnion consist of a single layer of epithelium cells, thin reticular fibers (basement membrane), a thick compact layer, and a fibroblast layer. The fibrous layer of amnion (i.e., the basement membrane) contains collagen types IV, V, and VII, and cell-adhesion bioactive factors including fibronectin and laminins. The amnion so recovered is commercially used in wound grafts which protect the wound and induce healing.

In addition to such beneficial uses, amnion has been found to act as a stem cell recruiter as provided in U.S. Patent Application Publication No. 2014/0106447, which is incorporated herein by reference in its entirety.

U.S. Patent Application Publication 2013/0344162 describes micronized placental tissue compositions and methods of making and using the same. U.S. patent application Ser. No. 13/903,878 describes biologically compatible polymer-chelator conjugates and methods of making and using the same. These references are incorporated herein by reference in their entirety.

Koob et al. have described methods of producing nordihydroguaiaretic acid (NDGA) polymerized and cross-linked collagen fibers for various biomedical applications, some with tensile strengths similar to that of natural tendon (e.g., about 91 MPa). See, for example, Koob and Hernandez, *Material properties of polymerized NDGA-collagen composite fibers: development of biologically based tendon constructs*, Biomaterials 2002 January; 23 (1): 203-12; and U.S. Pat. No. 6,565,960, the contents of which are hereby incorporated by reference as if recited in full herein.

SUMMARY OF THE INVENTION

This invention is directed to compositions comprising micronized placental tissue components, such as amnion, chorion, intermediate tissue layer and Wharton's jelly, as well as laminates thereof, and optionally a filler, wherein at least a portion of the placental components and/or the filler is conjugated to chelating moieties. Preferably, the chelating moieties have releaseably bound pharmacologically active metal ions such that the metal ions are released in a sustained manner over time. The actions of these metal ions can thereby be coupled with the therapeutic effects of micronized amnion in a localized manner to provide enhanced therapy.

Alternatively, the compositions of this invention can be used to kill or disrupt aberrant cells including aberrant stem cells. In such an embodiment, the compositions comprise placental components, such as amnion and chorion as well as laminates thereof, and optionally a filler. Either or both are coupled to a chelating agent having reversibly bound thereto pharmacologically active agent comprising one or more pharmacologically active metal ions such as cisplatin. In some embodiments, the amnion is used to recruit the aberrant stem cells such as cancer stem cells (CSCs) and the anti-cancer agents are used to kill or disrupt the CSCs. In this regard, CSCs are believed to be responsible for cancer recurrence, initiation, progression, metastasis, and drug resistance. Without being bound by theory, it is believed that introduction of a composition of the current invention at the site of a tumor will result in targeting of the CSCs by a metal-containing anticancer agent. That is to say, the CSCs will be recruited to the tumor site by the amnion and will be killed or inhibited by the anticancer agent.

In one of its composition aspects, the invention relates to a composition comprising micronized placental tissue and components thereof such as amnion, chorion and laminates thereof and optionally a filler wherein at least a portion of the micronized tissue and/or filler is conjugated to one or more chelating moieties. In addition, micronized umbilical cord materials such as micronized Wharton's jelly can be combined with the micronized placental tissue.

In another of its composition aspects, therapeutically active metal ions are releasably bound to the chelating moieties. In one aspect, the metal ions are anticancer agents which are released over time so as to provide sustained anticancer activity.

The placental composition, such as amnion, chorion, intermediate tissue layer, Wharton's jelly composition, of the invention may be introduced in a patient having cancer that is amenable to treatment with a metallic ion, for example, platinum alkylators. Such compositions may be introduced into the patient before, during, and/or after treatment of the tumor. In one aspect, the composition is introduced at or near the site of a tumor that is otherwise not treatable, for example, an inoperable brain tumor or spinal cord tumor. In one aspect, the composition is introduced at or near the site of a tumor in conjunction with other treatment, for example surgery, chemotherapy, and/or radiation therapy. In one aspect, the composition is introduced at or near the site of a tumor after the tumor has been treated and/or removed.

The chelating moiety can be any moiety with functional groups pendent thereto which are suitable for reversibly binding biologically compatible and pharmacologically active metal ions. Examples of such biologically compatible and pharmacologically active metal ions include, without limitation, ions of silver, copper, or a metallic ionic antitumor agent. Preferably, the anti-tumor agent is ionic platinum. The chelating moieties described herein can contain a mixture of metals such as anti-bacterial silver ions and/or anti-fungal copper ions to inhibit opportunistic bacterial and/or fungal infections at the site treated for cancer.

In one embodiment, the placental composition, such as amnion or chorion composition of the invention, is injected at or near the affected area. In one embodiment, the placental composition is implanted at or near the affected area. Without being bound by theory, it is believed that localized introduction of the composition reduces the potential side effects that occur with systemic treatment with pharmacologically active metal ions.

This invention is also directed to methods for making and using the compositions described herein having one or more chelating moieties bound thereto.

Several of the advantages of this invention are set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawing(s), which are incorporated in and constitute a part of this specification, illustrate several aspects described below.

In FIG. 2, the release rates of the metal ions from a chelating agent conjugate containing different non-cross-linking chelating agents (moieties) are illustrated. The release rates from these two different chelating agents are selected to overlap so as to provide a sustained release of the metal ion over time. In FIG. 3, the release rates of the metal ions from two similar conjugates are illustrated. In this case, the chelating moieties of the conjugates are selected so that their release rates do not to overlap. This results in release of a first bolus of metal ion release followed by release of a second bolus of metal ion.

DETAILED DESCRIPTION

Figure 1A:
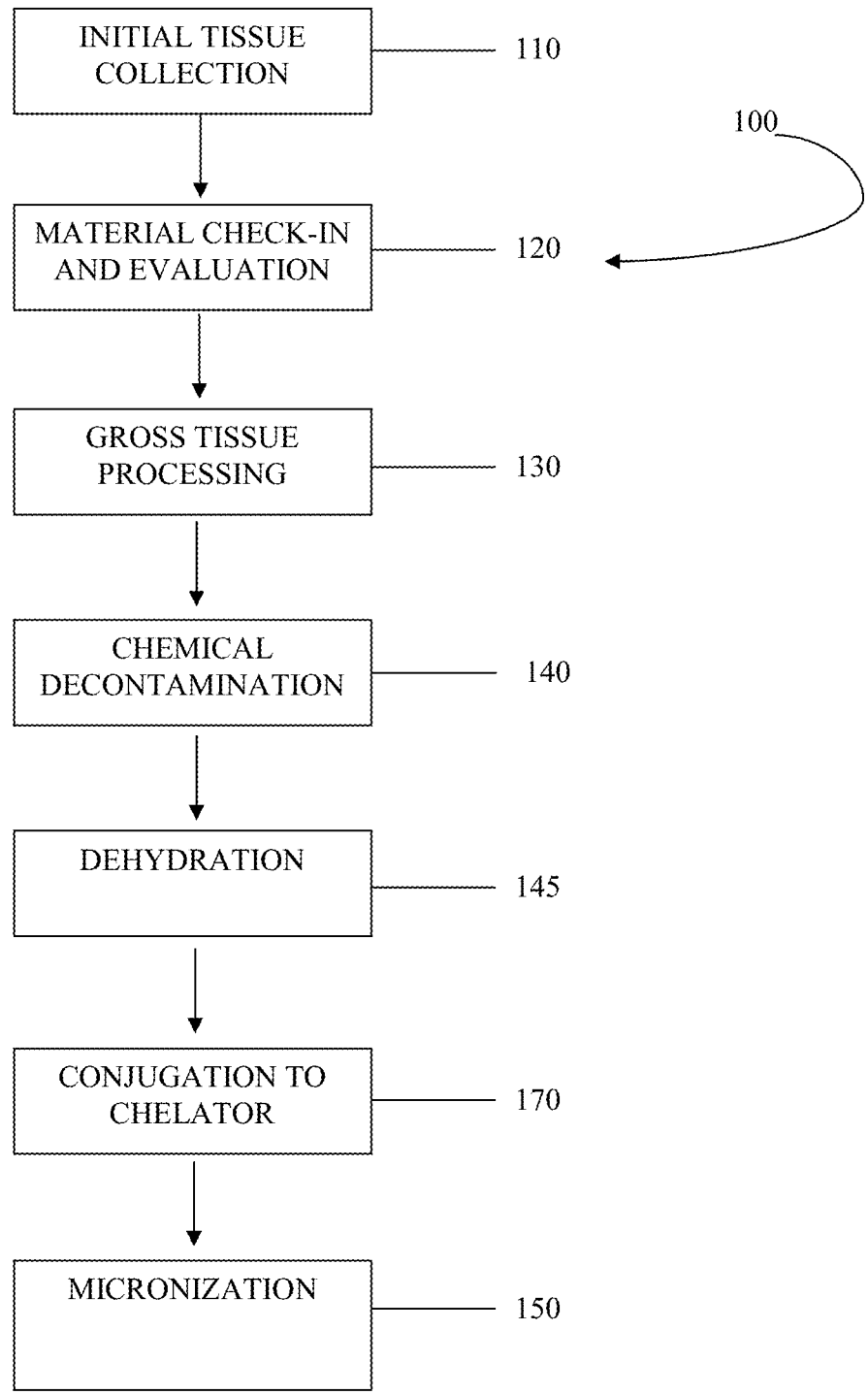
FIGS. 1A and 1B are overview flow charts of the process for making the amnion compositions described herein.

Before the present invention is disclosed and described, it is to be understood that the aspects described below are not limited to specific compositions, methods or preparing such compositions, or uses thereof as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

All numerical designations, e.g., pH, temperature, time, concentration, and weight, including ranges of each thereof, are approximations that typically may be varied (+) or (−) by increments of 0.1, 1.0, or 10.0, as appropriate. All numerical designations may be understood as preceded by the term "about".

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "amnion" as used herein includes amniotic membrane where the intermediate tissue layer is intact or has been substantially removed.

The term "amnion composition" refers to a composition comprising one or more placental tissue components wherein at least one of the components is amnion. The amnion composition optionally includes a filler. The term amnion composition further optionally includes one or more chelating agents bound to a component(s) of the composition.

The term "chorion composition" refers to a composition comprising one or more placental tissue components wherein at least one of the components is chorion. The chorion composition optionally includes a filler. The term chorion composition further optionally includes one or more chelating agents bound to a component(s) of the composition.

The term "filler" refers to any component of the composition other than amnion. Filler includes other placental tissue components as well as polymers, including collagen, hyaluronic acid, biocompatible plasticizers and the like. In one embodiment, the collagen include human collagen and collagen prepared from placental tissue, such as collagen materials substantially free of non-human antigens. In some embodiments, the collagen is prepared form the fibrous layer of amnion (i.e., the basement membrane) which contains collagen types IV, V, and VII. The collagen filler described herein is separate and apart from the collagen, if any, that exists in the placental component, such as in the amnion or chorion, of the composition. In some aspects, the collagen is free or substantially free of other components, including elastin, fibronectin, and/or laminin.

The term "non-human antigen" refers to any agent (e.g., protein, peptide, polysaccharide, glycoprotein, glycolipid, nucleic acid, or combination thereof) of non-human origin that, when introduced into a human, is immunogenic, eliciting an unwanted immune response that requires medical treatment for the manifestations (e.g., inflammation, etc.) of the immune response. As defined herein, the non-human antigen-induced immune response can be humoral or cell-mediated, or both.

The term "placental tissue" refers to any and all of the well-known components of the placenta including but not limited to amnion, chorion, intermediate tissue layer, umbilical cord component, such as Wharton's Jelly, and the like. In one embodiment, the placental tissue does not include any of the umbilical cord components (e.g., Wharton's jelly, umbilical cord vein and artery, and surrounding membrane). In another embodiment, the placental tissue includes any of the umbilical cord components (e.g., Wharton's jelly, umbilical cord vein and artery, and surrounding membrane).

The term "mold," "molded," or "molding" includes any form of molding such as the use of actual molds, extrusion under pressure, stamping or any pressurized method, and the like such that micronized placental tissue, and optionally filler, are compressed under pressure to produce a placental composition that has a defined size and shape for a defined period of time for use either ex vivo or in vivo. The molded placental composition preferably has a sufficient density and cohesiveness to maintain its size and shape during administration in vivo.

The term "comprising" means any recited elements are necessarily included and other elements may optionally be included. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

"$C_m$" when placed before a group refers to that group containing m carbon atom(s).

"Alkyl" refers to a hydrocarbyl radical, preferably monovalent, containing 1-12 carbon atoms. Non limiting examples of alkyl includes methyl, ethyl, propyl, isopropyl, butyl, isobutyl, tertiary butyl, and the like.

"Cycloalkyl" refers to a cyclic hydrocarbyl radical, preferably monovalent, containing 3-10 carbon atoms and includes bicyclic radicals. Non-limiting examples of cycloalkyl include cyproyl, cyclobutyl, cyclopentyl, cyclohexyl, and the like.

"Aryl" refers to an aromatic hydrocarbyl mono-, bi-, or tricyclic rings having from 6 to 14 carbon atoms.

"Heteroayl" refers to an aryl ring containing 1-5 ring heteroatoms selected from nitrogen, oxygen, sulfur, and appropriate oxidized forms thereof and having from 1 to 14 carbon atoms.

"Aldehyde" refers to a compound of formula O=C(H)—R wherein R is selected from the group consisting a chelating moiety connected to the aldehyde optionally through a linker moiety. When a linker is employed, the aldehyde is represented by the formula R-L-aldehyde and L is the linker.

"Isocyanate" refers to a compound of formula O=N=C-L-R where R is as defined above and L is a bond or a linker moiety.

The term "linker" defined above as "L" refers to a covalent bond or a linking group having 1 to 10 atoms selected from oxygen, sulfur, nitrogen and carbon atoms which links the chelating moiety to the placental component, such as amnion or chorion and/or the filler.

The term "chelating moiety" refers to well-known substituents which contain functional groups capable of chelating metal ions. Such substituents include by way of example only $\alpha$, $\beta$ groups such as hydroxyl groups, carboxyl groups, amino groups, or mixtures thereof (a carboxyl and a hydroxyl group). The chelating moiety reversibly bonds to the metal ion and the strength of the chelation is measured by a dissociation constant. The art is replete with different dissociation constants for binding different metal ions to specific and well characterized chelating moieties.

The term "subject" or "patient" as used herein refers to any vertebrate organism including, but not limited to, mammalian subjects such as humans, farm animals, domesticated pets and the like.

The term "biocompatible" as used herein refers to a material that is suitable for implantation or injection into a subject. In various aspects, a biocompatible material does not cause toxic or injurious effects once implanted in the subject.

The term "modified placental tissue" refers to any and all components of placental tissue including whole placental tissue that has been modified by cleaning, disinfecting, and/or segmenting the tissue as well as to separated components of placental tissue such as amnion, chorion, the umbilical cord, and the like. Modified tissue may maintain cellular layers, such as the epithelial layer and/or the fibroblast layer. Modified placental tissue may include further modification, such as lamination of one or more layers of placental tissue, micronization of placental tissue, chemisorption or physisorption of small molecules, proteins (e.g. growth factors, antibodies), nucleic acids (e.g. aptamers), polymers, or other substances.

The term "sufficient amount of" refers to an amount of a composition that is sufficient to have the desired effect, e.g. provoke stem cell recruitment proximate to or on the composition over time, either in vivo or in vitro. The "sufficient amount" of an placental composition, such as an amnion or chorion composition will vary depending on a variety of factors, such as but not limited to, the type and/or amount of placental composition used, the type and/or amount of filler used, the type and/or size of the intended organ and/or body part to be treated, the severity of the disease or injury to the organ and/or body part to be treated and the administration route. The determination of a "sufficient amount" can be made by one of ordinary skill in the art based on the disclosure provided herein.

As used herein, an "anticancer amount of metal ion" or "anticancer amount of anticancer agent" refers to an amount of anticancer agent, such as a metal ion, chelated to a composition of this invention that when contacted in vitro or in vivo with aberrant cells, for example cancer cells, inhibits or kills aberrant cells or tissue, and inhibits or kills, preferably, 50%, more preferably, 90%, and still more preferably 99% of such cells or tissue. As used herein, "effective amount of anticancer agent" refers to an amount of anticancer agent that is, preferably, released from a composition of this invention and that is sufficient to inhibit or kill, in vitro or in vivo, preferably, 50%, more preferably, 90%, and still more preferably 99% of aberrant cells or tissue. An effective amount of anticancer agent can improve one or more cancer symptoms, and/or ameliorate one or more cancer-side effects, and/or prevent and/or impede invasiveness and/or metastasis of cancer. In certain embodiments, an anticancer amount of anticancer agent can differ from an effective amount of anticancer agent.

The term "stem cell recruiting factors" refers to any and all factors that are capable of recruiting stem cells and causing them to migrate towards a source of such factors. Non-limiting examples of stem cell recruiting factors may be one or more CC chemokines, CXC chemokines, C chemokines, or CX3C chemokines.

The term "stem cell recruitment" refers to direct or indirect chemotaxis of stem cells to a placental composition, such as an amnion or chorion composition. The recruitment may be direct, wherein stem cell recruiting factors (e.g. chemokines, which induce cell chemotaxis) in an composition are released from the composition and induce stem cells to migrate towards the amnion composition. In one aspect, the recruitment may be indirect, wherein stem cell recruiting factors in the composition are released from the composition which induce nearby cells to release factors (e.g. chemokines), that in turn induce stem cells to migrate towards the composition. Still further, stem cell recruitment may embody both direct and indirect factors.

As used herein "cancer amenable to treatment with a metallic ion" refer to those cancers that are treated with one or more metallic ions, e.g. platinum alkylators, non-limiting examples of which include cisplatin, carboplatin, oxaliplatin, satraplatin, as are well known to the skilled artisan. Non-limiting examples of such cancers include non-small cell lung, breast, ovarian, testicular, prostate, and bladder cancer.

"Alkylators" or "alkylating agents" as used herein are agents that can alkylate, or transfer an electrophilic metal moiety, such as a platinum moiety to, nucleic acids and/or proteins as is well known to the skilled artisan. Alkylating agents may also be alkylating-like agents, which refers to agents that do not contain alkyl groups but have a mode of action similar to alkylating agents.

"Pharmacologically active agent comprising metal ions" refers to a substance containing an active mental ion, wherein the therapeutic effect of the agent, such as treatment of a disease, injury or condition, is at least in part due to the activity of the mental ion. Pharmacologically active agent comprising metal ions include platinum alkylating agents. "Pharmacologically active metal ion" refers to the active metal ion the pharmacologically active agent comprising metal ions, such as platinum ion, silver ion, copper ion, etc. Pharmacologically active metal ions are known in the art as antimicrobial agents and anticancer agents. U.S. Patent Application Publication Nos. US2014/0141096, US2014/0142041, and U.S. patent application Ser. Nos. 13/903,878, and 13/860,473 describe pharmacologically active metal ions and their uses. These references are incorporated herein by reference in their entirety.

The term "diseased" as used herein refers to an organ and/or body part that is characterized as being in a disease state, or susceptible to being in a disease state, wherein the disease is amenable to treatment with stem cells.

The term "injured" as used herein is used to have an ordinary meaning in the art, and includes any and all types of damage to an organ and/or body part, wherein the injury is amenable to treatment with stem cells.

The term "implantable" and derivatives thereof means the device can be inserted, embedded, grafted or otherwise acutely or chronically attached or placed in or on a subject.

Titles or subtitles may be used in the specification for the convenience of a reader, which are not intended to influence the scope of the present invention. Additionally, some terms used in this specification are more specifically defined below.

The term "treatment" or "treating", to the extent it relates to a disease or condition, includes preventing the disease or condition from occurring or reoccurring, inhibiting development of the disease or condition, reducing or eliminating the disease or condition, and/or relieving one or more symptoms of the disease or condition.

I. Compositions Comprising Micronized Placental and Chelators

Described herein are micronized placental composition, such as amnion or chorion compositions and/or filler with one or more chelating moieties bound thereto and pharmaceutical compositions thereof. Such compositions are prepared from micronized placental tissue components, which are described in International Patent Application WO2012/112410, as well as in U.S. provisional application Ser. Nos. 61/442,346, 61/543,995, and US2014/0050788. The contents of these applications are specifically incorporated by reference in their entireties. It is understood that the term "micronized" is meant to include micron and sub-micron sized placental tissue particles.

In one aspect, the invention is directed to a composition that includes (a) micronized amnion and optionally at least one of micronized chorion, intermediate tissue layer, or any combination thereof, (b) one or more chelating moieties, wherein the chelating moieties are covalently bound to the amnion, and optionally (c) a pharmaceutically acceptable excipient.

In one aspect, the invention is directed to a composition that includes (a) micronized chorion and optionally at least one of micronized amnion, intermediate tissue layer, or any combination thereof, (b) one or more chelating moieties, wherein the chelating moieties are covalently bound to the chorion, and optionally (c) a pharmaceutically acceptable excipient.

In one aspect, the invention is directed to a composition that includes (a) micronized laminated layers of placental tissues comprising two amnion layers, two chorion layers, or one amnion layer and one chorion layers, and optionally at least one of micronized amnion, intermediate tissue layer, or any combination thereof, (b) one or more chelating moieties, wherein the chelating moieties are covalently bound to the amnion and/or chorion, and optionally (c) a pharmaceutically acceptable excipient.

In another aspect, the invention is directed to a composition that includes (a) micronized amnion and optionally at least one of micronized chorion, intermediate tissue layer, or any combination thereof, (b) one or more fillers, and (c) one or more chelating moieties, wherein the chelating moieties are covalently bound to the amnion and/or the filler, and optionally (d) a pharmaceutically acceptable excipient.

In another aspect, the invention is directed to a composition that includes (a) micronized chorion and optionally at least one of micronized amnion, intermediate tissue layer, or any combination thereof, (b) one or more fillers, and (c) one or more chelating moieties, wherein the chelating moieties are covalently bound to the chorion and/or the filler, and optionally (d) a pharmaceutically acceptable excipient.

For example, the composition includes micronized amnion with one or more chelating moieties bound thereto, which can be used without the addition of any fillers, stabilizers, buffers, or pharmaceutical components. Alternatively, the composition includes micronized placental tissue and at least one pharmaceutical excipient such as a filler, a stabilizer, a buffer, a coloring agent, a disintegrating agent and the like and optionally one or more pharmaceutical components. Preferably, the coloring agent facilitates in locating and properly placing the placental tissue, which can be otherwise difficult to discern from normal tissue, to the intended treatment site. The disintegrating agent modifies the rate that the micronized placental tissue composition erodes or disintegrates in vivo after being introduced to a subject.

In an embodiment, an effective amount of a pharmacologically active metal ion is chelated to a component of the composition. In an embodiment, the pharmacologically active metal ion is an anticancer agent. In an embodiment, the pharmacologically active metal ion is platinum ion.

In an embodiment, the micronized placental composition, such as amnion or chorion composition is optionally molded and dehydrated. In one embodiment, the molded composition further comprises a filler. One or more chelating moieties may be bound to the amnion, filler, or both. As one of ordinary skill in the art would understand, the molded, dehydrated composition is compressed under pressure into any shape or size, as long as the molded placental tissue composition has a coherent mass having a certain density. Alternatively, the dehydrated micronized placental components are compressed into any mold having a desired shape or size such that the molded dehydrated placental tissue graft takes the shape and size of the mold. It is within the purview of one of ordinary skill in the art to select suitable molding material, such as silicone, resin, Teflon®, or stainless steel, to form a mold of desired shape and size. Examples of molded placental tissue and methods of making can be found in U.S. patent application Ser. No. 13/815,753, which is hereby incorporated by reference in its entirety.

The molded composition optionally further comprises a biologically compatible plasticizer. The type and amount of plasticizer can be determined based on the desired properties of the molded composition, for example strength, flexibility, hydrophobicity, or hydrophilicity.

Figure 1B:
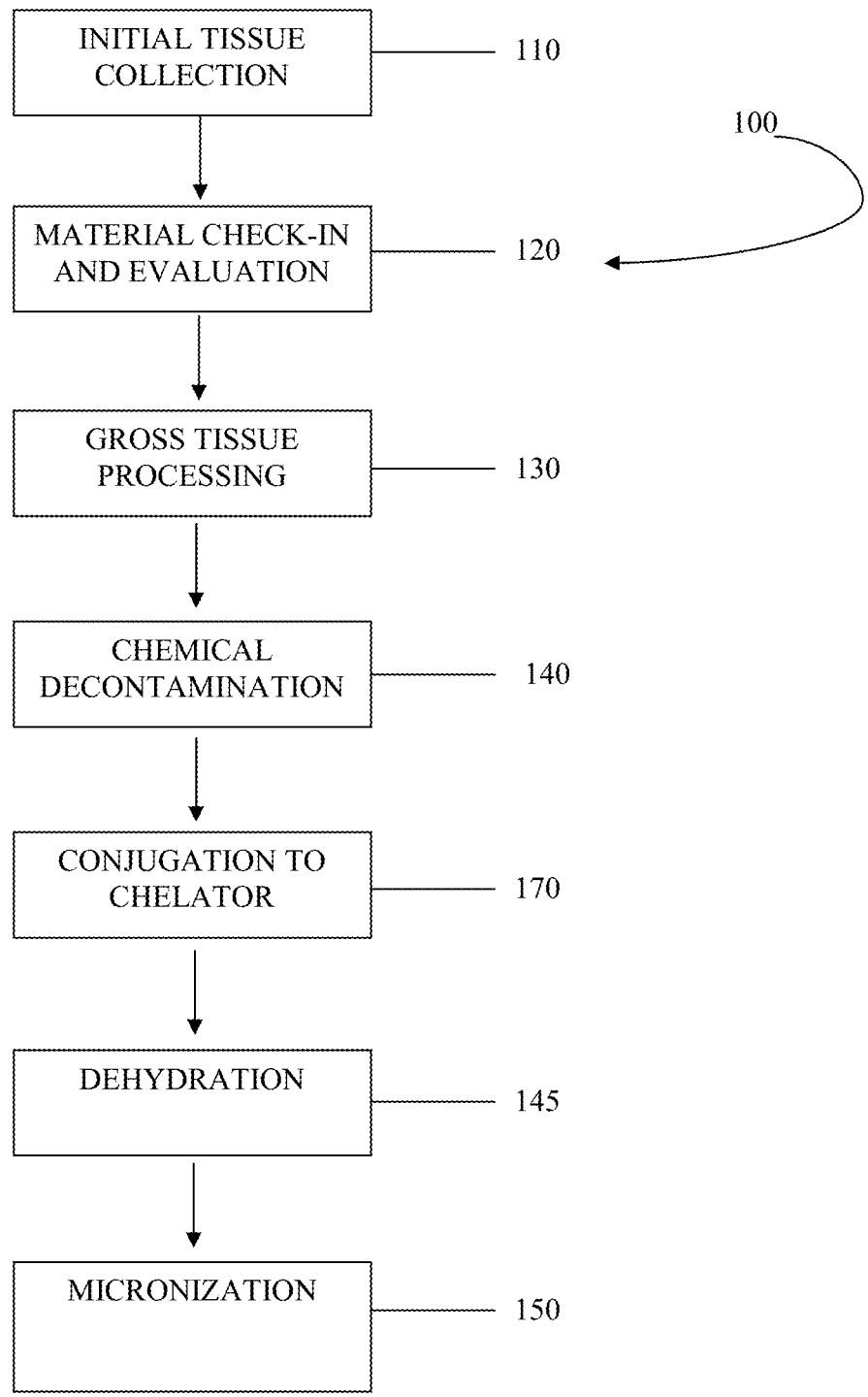

II. Methods of Making Placental Compositions with One or More Chelating Moieties Bound Thereto FIGS. 1A and 1B depict an overview (100) and certain aspects of the steps to harvest, process, and prepare dehydrated micronized placental material. More detailed descriptions and discussion regarding each individual step will follow. Initially, the placental tissue is collected from a consenting patient following an elective Cesarean surgery (step 110). The material is preserved and transported in conventional tissue preservation manner to a suitable processing location or facility for check-in and evaluation (step 120). Gross processing, handling, and separation of the tissue layers then takes place (step 130). Acceptable tissue is then decontaminated (step 140) and dehydrated (step 145). After decontamination and dehydration, the placental tissue components (e.g., amnion, intermediate tissue layer and/or chorion individually or as grafts) are then micronized (step 150). Chelators can be bound to the placental component (step 170) before (FIG. 1B) or after (FIG. 1A) dehydration or after micronization. Chelators may be bound to the filler at any step. Conjugation of the chelators to the placental component may optionally be performed after micronization. The micronized placental component and any other components are optionally compressed/molded under pressure into a desired shape or size. Each step is described in detail below.

Initial Tissue Collection (Step 110)

The components used to produce the placental composition described herein are derived from the placenta. The source of the placenta can vary. In one aspect, the placenta is derived from a mammal such as human and other animals including, but not limited to, cows, pigs, and the like can be used herein. In the case of humans, the recovery of the placenta originates in a hospital, where it is preferably collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), antibodies to the hepatitis B virus (anti-HBV) hepatitis B surface antigens (HBsAg), antibodies to the hepatitis C virus (anti-HCV), antibodies to the human T-lymphotropic virus type I and type II (anti-HTLV-I, anti-HTLV-II), CMV, and syphilis, and nucleic acid testing for human immune-deficiency virus type 1 (HIV-1) and for the hepatitis C virus (HCV), using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta is collected prior to the completion of obtaining the results from the screening tests and delivery cultures, such tissue is labeled and kept in quarantine. The placenta is approved for further processing only after the required screening assessments and delivery cultures, which declare the tissue safe for handling and use, are satisfied and final approval is obtained from a medical director.

Material Check-in and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing.

Gross Tissue Processing (Step 130)

When the tissue is ready to be processed further, the sterile supplies necessary for processing the placental tissue further are assembled in a staging area in a controlled environment and are prepared for introduction into a controlled environment. In one aspect, the placenta is processed at room temperature. If the controlled environment is a manufacturing hood, the sterile supplies are opened and placed into the hood using conventional sterilization techniques. If the controlled environment is a clean room, the sterile supplies are opened and placed on a cart covered by a sterile drape. All the work surfaces are covered by a piece of sterile drape using conventional sterilization techniques, and the sterile supplies and the processing equipment are placed onto the sterile drape, again using conventional sterilization techniques.

Processing equipment is decontaminated according to conventional and industry-approved decontamination procedures and then introduced into the controlled environment. The equipment is strategically placed within the controlled environment to minimize the chance for the equipment to come in proximity to or be inadvertently contaminated by the tissue specimen.

Next, the placenta is removed from the sterile shipment bag and transferred aseptically to a sterile processing basin within the controlled environment. The sterile basin contains hypertonic saline solution (e.g., 18% NaCl) that is at or near room temperature. The placenta is gently massaged to help separate blood clots and to allow the placental tissue to reach room temperature, which facilitates the separation of the placental components from each other (e.g., amnion membrane and chorion). After having warmed up to ambient temperature (e.g., after about 10-30 minutes), the placenta is then removed from the sterile processing basin and laid flat on a processing tray with the amnion membrane layer facing down for inspection.

The placenta is examined for discoloration, debris or other contamination, odor, and signs of damage. The size of the tissue is also noted. A determination is made, at this point, as to whether the tissue is acceptable for further processing.

The amnion and chorion are next carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion can be separated from the chorion. The amnion appears as a thin, opaque layer on the chorion.

The fibroblast layer is identified by gently contacting each side of the amnion with a piece of sterile gauze or a cotton tipped applicator. The fibroblast layer will stick to the test material. The amnion is placed into processing tray basement membrane layer down. Using a blunt instrument, a cell scraper, or sterile gauze, any residual blood is also removed. This step must be done with adequate care, again, so as not to tear the amnion. The cleaning of the amnion is complete once the amnion is smooth and opaque-white in appearance.

In certain aspects, the intermediate tissue layer, also referred to as the spongy layer, is substantially removed from the amnion in order to expose the fibroblast layer. The term "substantially removed" with respect to the amount of intermediate tissue layer removed is defined herein as removing greater than 90%, greater than 95%, or greater than 99% of the intermediate tissue layer from the amnion. This can be performed by peeling the intermediate tissue layer from the amnion. Alternatively, the intermediate tissue layer can be removed from the amnion by wiping the intermediate tissue layer with gauze or other suitable wipe. The resulting amnion can be subsequently decontaminated using the process described below.

In certain aspects, the epithelium layer present on the amnion is substantially removed in order to expose the basement layer of the amnion. The term "substantially removed" with respect to the amount of epithelium removed is defined herein as removing greater than 90%, greater than 95%, or greater than 99% of the epithelial cells from the amnion. The presence or absence of epithelial cells remaining on the amnion layer can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample is then covered and allowed to stand. Once an adequate amount of time has passed to allow for staining, visual observation is done under magnification.

The epithelium layer can be removed by techniques known in the art. For example, the epithelium layer can be scraped off of the amnion using a cell scraper. Other techniques include, but are not limited to, freezing the membrane, physical removal using a cell scraper, or exposing the epithelial cells to nonionic detergents, anionic detergents, and nucleases. The de-epithelialized tissue is then evaluated to determine that the basement membrane has not been compromised and remains intact. This step is performed after completion of the processing step and before the tissue has been dehydrated as described in the next section. For example, a representative sample graft is removed for microscopic analysis. The tissue sample is placed onto a standard slide, stained with Eosin Y and viewed under the microscope. If epithelium is present, it will appear as cobblestone-shaped cells.

The methods described herein do not remove all cellular components in the amnion. This technique is referred to in the art as "decellularization." Decellularization generally involves the physical and/or chemical removal of all cells present in the amnion, which includes epithelial cells and fibroblast cells. For example, although the removal of epithelial cells is optional, the fibroblast layer present in the amnion stromal layer is intact, even if the intermediate tissue layer is removed. Here, fibroblast cells are present in the fibroblast layer.

When the placental tissue is Wharton's jelly, the following exemplary procedure can be used. Using a scalpel or scissors, the umbilical cord is dissected away from the chorionic disk. Once the veins and the artery have been identified, the cord is dissected lengthwise down one of the veins or the artery. Once the umbilical cord has been dissected, surgical scissors and forceps can be used to dissect the vein and artery walls from the Wharton's jelly. Next, the outer layer of amnion is removed from the Wharton's jelly by cutting the amnion. Here, the outer membrane of the umbilical cord is removed such that Wharton's jelly is the only remaining component. Thus, the Wharton's jelly as used herein does not include the outer umbilical cord membrane and umbilical cord vessels. The Wharton's jelly can be cut into strips. In one aspect, the strips are approximately 1-4 cm by 10-30 cm with an approximate thickness of 1.25 cm; however, other thicknesses are possible depending on the application.

Chemical Decontamination (Step 140)

The placental tissue can be chemically decontaminated using the techniques described below. In one aspect, the amnion is decontaminated at room temperature. In one aspect, the amnion produced in step 130 (e.g., with or without the intermediate tissue layer) can be placed into a sterile Nalgene jar for the next step. In one aspect, the following procedure can be used to clean the amnion. A Nalgene jar is aseptically filled with 18% saline hypertonic solution and sealed (or sealed with a top). The jar is then placed on a rocker platform and agitated for between 30 and 90 minutes, which further cleans the amnion of contaminants. If the rocker platform was not in the critical environment (e.g., the manufacturing hood), the Nalgene jar is returned to the controlled/sterile environment and opened. Using sterile forceps or by aseptically decanting the contents, the amnion is gently removed from the Nalgene jar containing the 18% hypertonic saline solution and placed into an empty Nalgene jar. This empty Nalgene jar with the amnion is then aseptically filled with a pre-mixed antibiotic solution. In one aspect, the premixed antibiotic solution is composed of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the amnion. This jar or container containing the amnion and antibiotics is then sealed or closed and placed on a rocker platform and agitated for, preferably, between 60 and 90 minutes. Such rocking or agitation of the amnion within the antibiotic solution further cleans the tissue of contaminants and bacteria. Optionally, the amnion can be washed with a detergent. In one aspect, the amnion can be washed with 0.1 to 10%, 0.1 to 5%, 0.1 to 1%, or 0.5% Triton-X wash solution.

If the rocker platform was not in the critical environment (e.g., the manufacturing hood), the jar or container containing the amnion and antibiotics is then returned to the critical/sterile environment and opened. Using sterile forceps, the amnion is gently removed from the jar or container and placed in a sterile basin containing sterile water or normal saline (0.9% saline solution). The amnion is allowed to soak in place in the sterile water/normal saline solution for at least 10 to 15 minutes. The amnion may be slightly agitated to facilitate removal of the antibiotic solution and any other contaminants from the tissue. After at least 10 to 15 minutes, the amnion is ready to be dehydrated and processed further.

In the case of chorion, the following exemplary procedure can be used. After separation of the chorion from the amnion and removal of clotted blood from the fibrous layer, the chorion is rinsed in 18% saline solution for 15 minutes to 60 minutes. During the first rinse cycle, 18% saline is heated in a sterile container using a laboratory heating plate such that the solution temperature is approximately 48° C. The solution is decanted, the chorion tissue is placed into the sterile container, and decanted saline solution is poured into the container. The container is sealed and placed on a rocker plate and agitated for 15 minutes to 60 minutes. After 1 hour agitation bath, the chorion tissue was removed and placed into second heated agitation bath for an additional 15 minutes to 60 minutes rinse cycle. Optionally, the chorion tissue can be washed with a detergent (e.g., Triton-X wash solution) as discussed above for the decontamination of amnion. The container is sealed and agitated without heat for 15 minutes to 120 minutes. The chorion tissue is next washed with deionized water (250 ml of DI water×4) with vigorous motion for each rinse. The tissue is removed and placed into a container of 1×PBS w/EDTA solution. The container is sealed and agitated for 1 hour at controlled temperature for 8 hours. The chorion tissue is removed and rinsed using sterile water. A visual inspection was performed to remove any remaining discolored fibrous blood material from the chorion tissue. The chorion tissue should have a cream white visual appearance with no evidence of brownish discoloration.

The following exemplary procedure can be used when the placental tissue is Wharton's jelly. The Wharton's jelly is transferred to a sterile Nalgene jar. Next, room temperature 18% hypertonic saline solution is added to rinse the tissue and the jar is sealed. The jar is agitated for 30 to 60 minutes. After incubation, the jar is decontaminated and returned to the sterile field. The tissue is transferred to a clean sterile Nalgene jar and prewarmed (about 48° C.) with 18% NaCl. The container is sealed and placed on rocker plate and agitated for 60 to 90 minutes.

After the rinse, the jar is decontaminated and returned to the sterile field. The tissue is removed and placed into an antibiotic solution. The container is sealed and agitated for 60 to 90 minutes on a rocker platform. Following incubation, the jar may be refrigerated at 1° C. to 10° C. for up to 24 hours.

The Wharton's jelly is next transferred to a sterile basin containing approximately 200 mL of sterile water. The tissue is rinsed for 1-2 minutes and transferred to a sterile Nalgene jar containing approximately 300 ml of sterile water. The jar is sealed and placed on the rocker for 30 to 60 minutes. After incubation, the jar is returned to the sterile field. The Wharton's jelly should have a cream white visual appearance with no evidence of brownish discoloration.

Dehydration (Step 145)

In one aspect, the placental tissue or components thereof as described above, or any combination thereof, can be processed into tissue grafts (i.e., laminates) that are subsequently micronized. In another aspect, the placental tissue or individual components thereof can be dehydrated independently and subsequently micronized alone or as a mixture of components. In one aspect, the tissue (i.e., individual membrane or graft) is dehydrated by chemical dehydration followed by freeze-drying. In one aspect, the chemical dehydration step is performed by contacting the amnion, chorion, and/or intermediate layer with a polar organic solvent for a sufficient time and amount in order to substantially (i.e., greater than 90%, greater than 95%, or greater than 99%) or completely remove residual water present in the tissue (i.e., dehydrate the tissue). The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the placental tissue is contacted with a polar organic solvent at room temperature. No additional steps are required, and the tissue can be freeze-dried directly as discussed below.

After chemical dehydration, the tissue is freeze-dried in order to remove any residual water and polar organic solvent. In one aspect, the amnion, chorion, and/or intermediate layer can be laid on a suitable drying fixture prior to freeze-drying. For example, one or more strips of amnion can be laid on a suitable drying fixture. Next, chorion is laid on top of the amnion. In this aspect, an amnion/chorion tissue graft is produced. Alternatively, a strip of amnion can be placed on a first drying fixture, and a strip of chorion can be placed on a second drying fixture. The drying fixture is preferably sized to be large enough to receive the placental tissue, fully, in laid out, flat fashion. In one aspect, the drying fixture is made of Teflon® or of Delrin®, which is the brand name for an acetal resin engineering plastic invented and sold by DuPont and which is also available commercially from Werner Machine, Inc. in Marietta, Ga. Any other suitable material that is heat and cut resistant, capable of being formed into an appropriate shape to receive wet tissue can also be used for the drying fixture.

Once the tissue is placed on the drying fixture, the drying fixture is placed in the freeze-dryer. The use of the freeze-dryer to dehydrate the tissue can be more efficient and thorough compared to other techniques such as thermal dehydration. In general, it is desirable to avoid ice crystal formation in the placental tissue as this may damage the extracellular matrix in the tissue. By chemically dehydrating the placental tissue prior to freeze-drying, this problem can be avoided.

In another aspect, the dehydration step involves applying heat to the tissue. In one aspect, the amnion, chorion, and/or intermediate layer is laid on a suitable drying fixture (either as individual strips or as a laminate discussed above), and the drying fixture is placed in a sterile Tyvek® (or similar, breathable, heat-resistant, and sealable material) dehydration bag and sealed. The breathable dehydration bag prevents the tissue from drying too quickly. If multiple drying fixtures are being processed simultaneously, each drying fixture is either placed in its own Tyvek® bag or, alternatively, placed into a suitable mounting frame that is designed to hold multiple drying frames thereon and the entire frame is then placed into a larger, single sterile Tyvek® dehydration bag and sealed.

The Tyvek® dehydration bag containing the one or more drying fixtures is then placed into a non-vacuum oven or incubator that has been preheated to approximately 35 to 50 degrees Celsius. The Tyvek® bag remains in the oven for between 30 to 120 minutes. In one aspect, the heating step can be performed at 45 minutes at a temperature of approximately 45° C. to dry the tissue sufficiently but without over-drying or burning the tissue. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

In one aspect, the placental tissue can be dehydrated using a dehydration device which enhances the rate and uniformity of the dehydration process. Representative dehydration device suitable for drying placental tissue grafts are described in U.S. Patent publication No. 2014/0051059. The contents of this application is incorporated by reference in their entireties.

Preparation of Micronized Placental Components (Step 150)

Once the placental tissue or components thereof as described above have been dehydrated individually or in the form of tissue graft, the dehydrated tissue(s) is micronized. The micronized placental components can be produced using instruments known in the art. For example, the Retsch Oscillating Mill MM400 can be used to produce the micronized compositions described herein. The particle size of the materials in the micronized composition can vary as well depending upon the application of the micronized composition. In one aspect, the micronized composition has particles that are less than 500 µm, less than 400 µm, less than 300 µm, less than 200 µm, less than 100 µm, less than 50 µm, less than 25 µm, less than 20 µm, less than 15 µm, less than 10 µm, less than 9 µm, less than 8 µm, less than 7 µm, less than 6 µm, less than 5 µm, less than 4 µm, less than 3 µm, less than 2 µm, or from 2 µm to 400 µm, from 25 µm to 300 µm, from 25 µm to 200 µm, or from 25 µm to 150 µm. In one aspect, the micronized composition has particles that have a diameter less than 150 µm, less than 100 µm, or less than 50 µm. In other aspects, particles having a larger diameter (e.g. 150 µm to 350 µm) are desirable. In all cases, the diameter of the particle is measured along its longest axis.

In one embodiment, the size of the particles may be reduced to nano-range. As one skilled in the art would understand, nanoparticles of placental components may be desirable for the increased density and/or increased release rate upon applying to the wound. Preferably, the particle size of the micronized particles is from about 0.05 µm to about 2 µm, from about 0.1 µm to about 1.0 µm, from about 0.2 µm to about 0.8 µm, from about 0.3 µm to about 0.7 µm, or from about 0.4 µm to about 0.6 µm. Alternatively, the particle size of the micronized particles is at least 0.05 µm, at least 0.1 µm, at least 0.2 µm, at least 0.3 µm, at least 0.4 µm, at least 0.5 µm, at least 0.6 µm, at least 0.7 µm, at least 0.8 µm, at least 0.9 µm, or at least 1 µm. Alternatively, the particle size of the micronized particles is less than 1 µm, less than 0.9 µm, less than 0.8 µm, less than 0.7 µm, less than 0.6 µm, less than 0.5 µm, less than 0.4 µm, less than 0.3 µm, less than 0.2 µm, less than 0.1 µm, or less than 0.05 µm.

In one aspect, the initial micronization is performed by mechanical grinding or shredding. In another aspect, micronization is performed by cryogenic grinding. In this aspect, the grinding jar containing the tissue is continually cooled with liquid nitrogen from the integrated cooling system before and during the grinding process. Thus, the sample is embrittled and volatile components are preserved. Moreover, the denaturing of proteins in the amnion, intermediate tissue layer, and/or chorion is minimized or prevented. In one aspect, the CryoMill manufactured by Retsch can be used in this aspect.

The selection of components used to make the placental composition, such as amnion or chorion composition described herein can vary depending upon the end-use of the placental tissue composition For example, placental tissue or individual components such as amnion, chorion, intermediate tissue layer, Wharton's jelly or any combination thereof can be admixed with one another and subsequently micronized. In another aspect, one or more tissue grafts composed of one or more placental tissue, amnion, chorion, intermediate tissue layers, or any combination thereof (i.e., laminates) can be micronized. In a further aspect, one or more tissue grafts composed of one or more amnion, chorion, intermediate tissue layers, or any combination can be admixed with amnion, chorion, intermediate tissue layer, or any combination thereof as individual components and subsequently micronized.

The amount of different components can vary depending upon the application of the amnion composition. In one aspect, the amnion composition is composed solely of amnion (with or without the intermediate tissue layer). In one aspect, when the amnion composition is composed of amnion (with or without the intermediate tissue layer) and intermediate tissue layer, the weight ratio of amnion to intermediate tissue layer is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1. In another aspect, when the amnion composition is composed of amnion (with or without the intermediate tissue layer) and chorion, the weight ratio of chorion to amnion is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1.

Separation of particle sizes can be achieved by fractionation of the micronized material in sterile water by forming a suspension of particles. The upper most portion of the suspension will contain predominantly the smallest particles and the lower most portion of the suspension will contain predominantly the heaviest particles. Alternatively, the micronized material can be fractionated using sieves of the desired size(s). Fractionation leads to particle size separation and repeated fractionation will lead to separation of the micronized particles into varying sizes. The so separated particles can be recombined in the desired ratio of particle size as is most appropriate for making the amnion composition and the desired medical application.

Fillers

In some aspects, the compositions of the present invention comprise one or more fillers. In some aspects, the fillers are biocompatible polymers. Suitable polymers include those that are known in the art and are capable of forming chelator conjugates as described herein. Preferred biocompatible polymers useful in this invention include biodegradable polymers.

Suitable polymers include, without limitation, naturally-occurring polymers, synthetic polymers or mixtures thereof. In one embodiment, the polymer includes collagen (such as human collagen) or collagen prepared from placental tissue, e.g., amnion or chorion containing collagen. Other examples of naturally-occurring biocompatible polymers include, but are not limited to, hylauronic acid, fibrin, fibrous or globular proteins, complex carbohydrates, glycosaminoglycans, such as, or mixtures thereof. Thus, in one embodiment, the polymer may include collagens of all types, elastin, laminin, hyaluronic acid, alginic acid, desmin, versican, fibrin, fibronectin, vitronectin, albumin, and the like. Exemplary synthetic biocompatible polymers include, but are not limited to, polyoxyalkylenes (e.g., polyoxyethylene, polyoxypropylene, copolymers of oxyethylene and oxypropylene, and the like), polyethylene glycol, polymethylene glycol, polytrimethylene glycols, polyvinylpyrrolidones, caprolactones, 2-hydroxyethyl methacrylate (HEMA), silicone such as Nusil MED-6215 or other silicone suitable for implantation, poly(epsilon-caprolactone) dimethylacrylate, polysulfone, (poly)methyl methacrylate (PMMA), soluble Teflon-AF, poly ethylene teraphthalate (PET, Dacron), Nylon, polyvinyl alcohol, polyurethane, hydroxyapatite, and the like and mixtures thereof. Such polymers preferably have an average molecular weight of at least about 10,000 and more preferably from about 10,000 to about 1,000,000. In some embodiments, these polymers preferably have an average molecular weight of at least 10,000 and more preferably from about 10,000 to about 100,000. The polymers described herein can be either cross-linked with non-chelating agents or non-cross-linked. Common non-chelating cross-linking agents include carbodimides, diisothiocyanates, dicarboxylic acids, diamines and the like.

In some embodiments, the biocompatible polymers are water soluble polymers and are sometimes referred to as hydrophilic polymers. Water solubility can be achieved incorporating a sufficient number of oxygen (or less frequently nitrogen) atoms available for forming hydrogen bonds in aqueous solution. Hydrophilic polymers include, without limitation, polyoxyethylene, polyethylene glycol, polymethylene glycol, polytrimethylene glycols, polyvinylpyrrolidones, or derivatives thereof. The polymers are preferably linear or only slightly branched (i.e., having only about 2-10 significant free ends), and will not be substantially cross-linked. Other suitable polymers include polyoxyethylene-polyoxypropylene block polymers and copolymers.

Polyoxyethylene-polyoxypropylene block polymers having an ethylene diamine nucleus (and thus having four ends) are also available and may be used in the practice of the invention. Hydrophilic polymers can also include naturally occurring polymers such as proteins (e.g., and without limitation, a collagen), starch, cellulose, and the like.

All suitable polymers are biocompatible, and preferably non-toxic and non-inflammatory when administered in vivo, and will more preferably be degradable in vivo with a degradation time of at least several months.

In some embodiments, the polymers have at least one and preferably up to 1000 reactive functionalities which are complementary to the reaction functionalities on the precursor chelator compound. Typically, the complementary reactive functionality is present on the polymer such as reactive functionalities found in collagen, hyaluronic acid, and the like or can be introduced onto the polymer by conventional chemical synthetic techniques well known to the skilled artisan. Exemplary functionalities include, without limitation, amine, carboxylic acid, hydrazine, hydrazone, azide, isocyanate, isothiocyanate, alkoxyamine, aldehyde, epoxy, nitrile, maleimide, halo, hydroxyl, thiol or a combination thereof. Preferably, the reactive functional group is selected from the amine or carboxylic acid. Complementary functionalities include those that react with each other to form a covalent bond. Examples include isocyanates with amines and hydroxyl groups to form a urea or carbamate linkage, carboxylic acids and amines which form amides, and the like. The following table illustrates some common complementary reactive groups, one of which is found on the precursor chelating moiety (first reactive functionality) and the other on the polymer (second reactive functionality).

| First reactive functionality | Second reactive functionality | Covalent Bond formed |
|---|---|---|
| Amine | Carboxyl | Amide |
| Hydroxyl | Halide | Ether |
| Isocyanate | Amine | Urea |
| Isocyanate | Hydroxyl | Carbamate |
| Carboxyl | Amine | Amide |
| Thioisocyanate | Hydroxyl | Thiocarbamate |

The polymers can be functionalized, for example, by introducing an amine-functional monomer, either pendant or terminal to the polymer. A suitable method for imparting a pendant amine functionality to the polymer is to use a monomer containing a pendant amine functionality. Suitable monomers containing a pendant amine functionality include 2-aminoethylacrylate, 2-aminoethylmethacrylate, 2-aminoethylacrylamide, 2-amino ethylmethacrylamide, dimethylaminoethylmethacryl, aminopropyl (meth)acrylamide and the like. When a monomer containing a pendant amine functionality is used, the resulting polymer may contain one or more pendant amine groups. Preferably, the pendant amine functionality which is imparted to the polymer is a terminal pendant amine functionality. Terminal pendant amine functionality can be imparted to a polymer by using one or more compounds which, when they function as a chain transfer agent, have a pendant amine group. Preferred compounds for imparting terminal amine functionality are amine-thiols, e.g., N-butylaminoethanethiol, N,N-diethylaminoethanethiol and salts thereof.

Likewise, the polymers of the invention can be functionalized, for example, by introducing a carboxylic acid-functional monomer. Preferred acid monomers are carboxylic acids or their derivatives, including, but not limited to, monounsaturated monocarboxylic acid, monounsaturated dicarboxylic acid, anhydrides or alcohol derived mono- or di-esters. Upon reaction with the polymer, e.g., a polyolefin, the monounsaturation of the monounsaturated carboxylic reactant becomes saturated. Exemplary monounsaturated carboxylic reactants include fumaric acid, itaconic acid, maleic acid, maleic anhydride, chloromaleic acid, chloromaleic anhydride, acrylic acid, methacrylic acid, crotonic acid, cinnamic acid, and lower alkyl acid esters, such as methyl maleate, ethyl fumarate, and methyl fumarate. In other embodiments, polymer containing anhydride or ester functionality can be converted by well known hydrolysis methods to acid.

Chelators

A variety of chelators well known for binding various pharmacologically active metal ions, such as ions of copper, silver, and platinum, are useful in the present invention; preferably such chelators are biocompatible. Biocompatible chelators are described, for example, in U.S. Patent Application Ser. No. 61/728,198 and U.S. Patent Application Publication No. 2014/0142041, both of which are incorporated herein by reference in their entireties.

Suitable chelators preferably comprise one or more $C_2$-$C_{10}$ alkyl or heteroalkyl, $C_6$-$C_{10}$ aryl $C_3$-$C_{10}$ heteroaryl, or $C_5$-$C_{10}$ cycloalkyl groups substituted with at least two, adjacent (or 1,2 substituted) hydroxy, $C_2$-$C_{10}$ alkoxy, amino, ($C_2$-$C_{10}$) alkylamino, ($C_2$-$C_{10}$)$_2$dialkylamino, mercapto, $C_2$-$C_{10}$ thioalkyl groups, which alkyl or heteroalkyl, aryl, heteroaryl, or cycloalkyl groups are attached via a linker, or a bond and a functional joining group, to the amnion and/or filler.

The term "chelator precursor compound" refers to the chelator prior to reaction with the amnion composition or filler. The precursor compound contains a reactive functionality which reacts with a complementary functionality on the amnion or filler to form a covalent bond. The resulting chelating moiety is referred to as the "chelator" and is defined above. The reactive functional groups on the chelator precursor compounds form a stable covalent bond when coupled with the complementary reactive functional group on the amnion or filler. Such stable covalent bonds include by way of example esters, ethers, amides (—CONH—, —NHCO—, —N(alkyl)CO— or CO—N(alkyl)-), carbamates, urea, carbonate, thiocarbonate, thiourea, carbamate, and urethane bonds, as well as any other well-known covalent bonds. Reactive functional groups either on the chelator precursor compound, the amnion, or the filler include those such as amino, hydroxy, mercapto, and carboxylic acid, carboxylate esters, isocyanate, and other well-known functional groups that can be chemically bonded following art known methods to a complementary reactive functional group on the amnion or filler as utilized herein. The group X on the chelator precursor compound is selected from the group consisting of H or a complimentary reactive functional group. It is understood that when X is a complimentary functional group the other functional groups on the compound may need to be blocked or protected using conventional methods and protecting groups.

In one embodiment, the chelating agent comprises a 1,2-benzoquinone and/or a 1,2-dihydroxy phenyl moiety. In another embodiment, the chelating moiety is derived from a precursor compound selected from the group consisting of nordihydroguaiaretic acid (NDGA), 3,4-dihydroxyphenylalanine, dopamine, 3,4-dihydroxybenzaldehyde, and 3,4-dihydroxybenzoic acid.

In one embodiment, the chelating agent is derived from a precursor compound which can both react with and form a covalent bond to amnion and/or filler and reversibly bind the pharmacologically active metal ion. Preferably, the precursor compound is selected from the group consisting of:

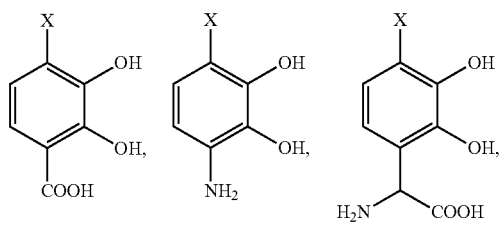

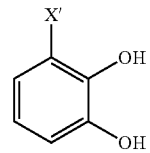

wherein X is H or a complimentary reactive functional group, such that when X is a complimentary reactive functional group, the other functional groups on the molecule are protected.

In one embodiment, the precursor compound is:

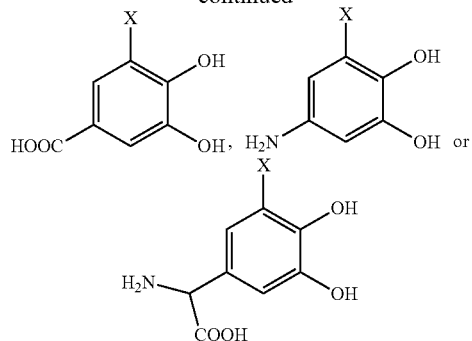

where X' is a complimentary reactive functional group, such that the hydroxyl groups on the molecule are optionally protected.

Preferable chelating agents used are derived from naturally occurring compounds such as dopamine and L-dopa.

After reaction, the chelator is sometimes referred to a chelating agent or as a chelating moiety.

Pharmacologically Active Metal Ions

Suitable pharmacologically active metals are known in the art. In one embodiment, the pharmacologically active metal is an anticancer agent. Anticancer metals include, without limitation, platinum, ruthenium, osmium and cobalt. As used herein, the term "anticancer agent" or "anticancer metal ion" refers to any metal ion-containing compound that can improve one or more cancer symptoms, and/or ameliorate one or more cancer-side effects, and/or prevent and/or impede invasiveness and/or metastasis of cancer.

Anticancer agents are detailed in U.S. Patent Application Publication No. 2014/0142041, which is incorporated by reference in its entirety. In one embodiment, the metal ion is ionic platinum. In one embodiment, the platinum comprises platinum (II) and/or platinum (IV). In another embodiment, the platinum comprises a compound selected from the group of

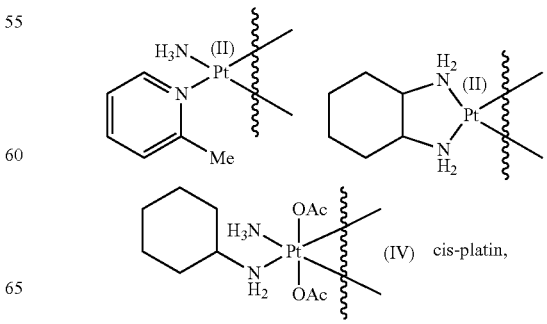

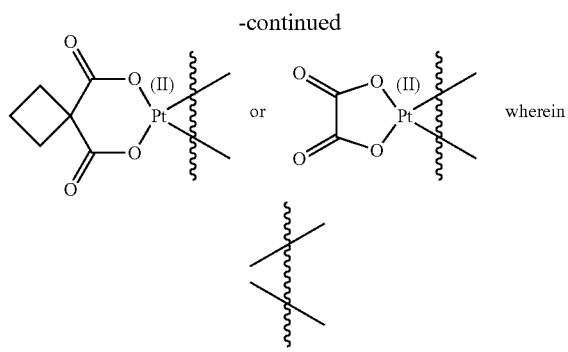

denotes binding to the chelator.

The chelated amnion-Pt and/or filler-Pt constructs of this invention are prepared by contacting appropriate Pt salts, preferably, Pt(II) salts with a functionalized amnion composition or filler of this invention. Preferably, the Pt salt is a cis diamino Pt(II) dichloro or, yet more preferably, a cis diamino Pt(II) diaqua salt. An illustrative and non-limiting example is shown below:

Step A

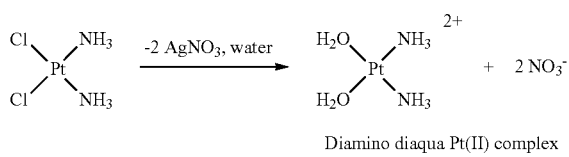

Diamino diaqua Pt(II) complex

Step B

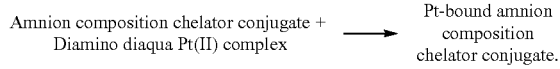

Figure 2:
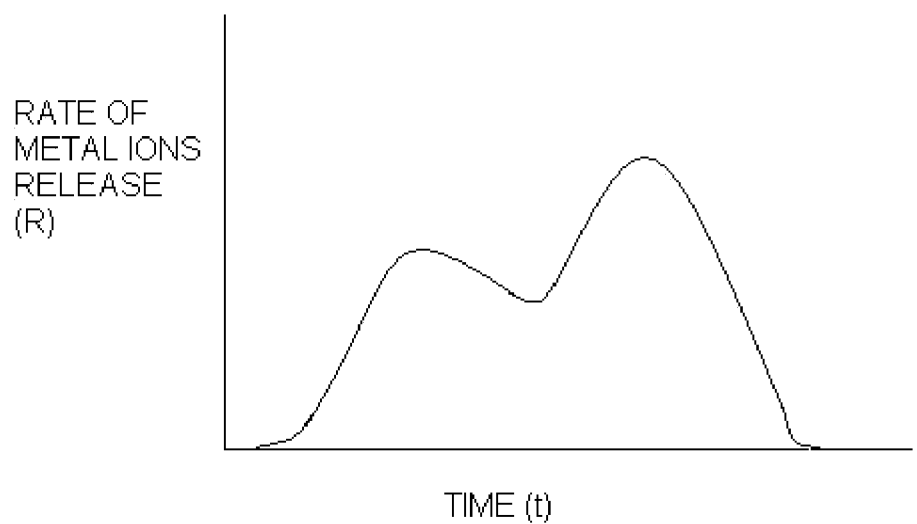
FIGS. 2 and 3 illustrate different binary release patterns of metallic ions from a composition comprising a mixture of amnion- or filler-chelating agent conjugates using different chelating moieties.
Figure 3:
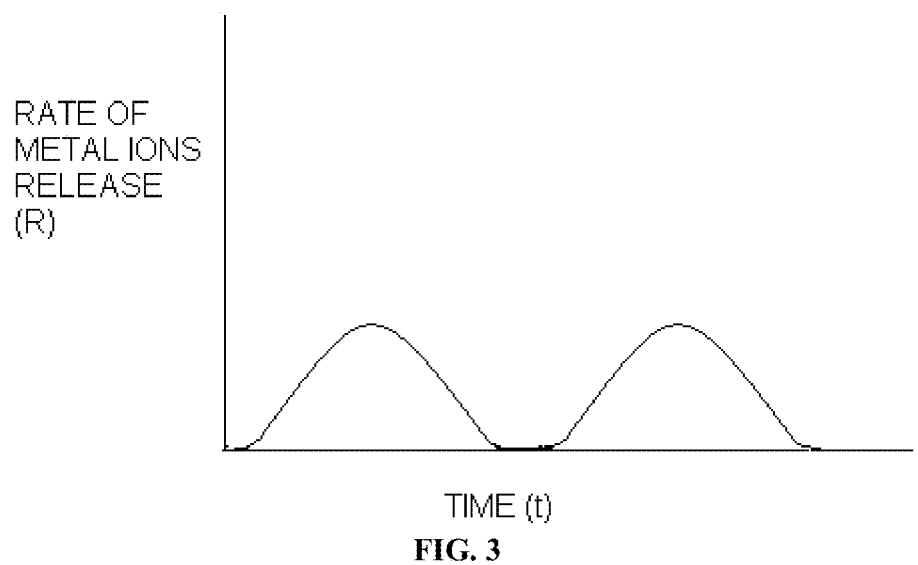

Excess Pt salts, not bound to the amnion composition or filler of this invention, can be removed by complexing with a resin, such as Chelex. An amnion composition-Pt(II) or filler-Pt(II) construct can be converted to the corresponding Pt(IV) construct by oxidation, for example with $H_2O_2$. FIGS. 2 and 3 illustrate the use of different conjugates in a manner where the release rates of the conjugates overlap (FIG. 2) so as to provide a continuous release of the metal ion whereas FIG. 3 illustrates the use of different conjugates in a manner where the release rates do not overlap so as to provide two separate releases (bolus) of metal ion.

As used herein, a cis-diaqua platinum complex contains 2 water molecules bound to platinum in cis or adjacent configuration, and a cis-dihalo platinum complex contains 2 halogen, preferably chloride groups, bound to platinum in cis or adjacent configuration.

Polymer Conjugates

The polymer constructs of this invention are described below using collagen as an exemplary polymer. It is understood, however, that polymers other than collagen, such as those described herein, can be utilized in place of collagen. Exemplary biocompatible collagen conjugates and devices made therefrom are described in U.S. Pat. No. 7,901,455; U.S. Patent Application Publication Nos. 2008/0161917, 2008/0188933, 2008/0200992, 2009/0216233, 2009/0287308, 2010/0094318, 2010/0094404, 2011/0282448, 20110282447 and 2014/0172096, which are incorporated herein by reference.

The conjugates of the present invention can be dry or partially hydrated. The term "dry" as used herein means the construct has a moisture content of less than about 5% by weight of the construct. The term "partially hydrated" as used herein means that the construct has a moisture content that is less than about 50%, typically less than about 75% of the moisture content at full hydration, measured ex vivo after 24 hours in a saline bath at ambient conditions. Thus, the construct can have a moisture content of less than about 25% by weight of the construct, such as less than about 15% by weight of the construct.

Preparation of Molded Placental Grafts and Pharmaceutical Compositions Thereof (Optional)

The amnion composition of the current invention may optionally be a molded placental graft. The dehydrated components, such as micronized amnion, micronized chorion, micronized intermediate tissue layer, filler, and any combination thereof, when subjected to pressure preferably in a non-porous mold, form a desired shape and size defined by the mold. While a porous mold is less preferred, it is contemplated that such can be used in the methods of this invention if water or other solvents are allowed to escape during molding. The molded amnion graft has a sufficient density and cohesive mass to maintain its size and shape at least until the molded amnion graft is introduced to a subject. The cohesion of the molded amnion graft is determined, in part, by the particle size of the micronized components. For example, micronized components having larger particle size require higher compressive pressure and/or longer compression time to obtain a molded amnion graft having the same density as that of a molded amnion graft composed of micronized components having smaller particle size. In other words, for molded compositions obtained under the same compression condition, the compositions having larger particle size have less density and dissociate at a higher rate in comparison to the compositions having smaller particle size.

Optionally, one or more adhesives can be admixed with the placental composition, such as amnion or chorion composition prior to being introduced into the mold. Examples of such adhesives include, but are not limited to, fibrin sealants, cyanoacrylates, gelatin and thrombin products, polyethylene glycol polymer, albumin, and glutaraldehyde products. The adhesives used in the process should be dehydrated prior to being mixed with the placental composition such that the mixture of adhesives and placental composition has a sufficiently low water content to permit compression in a non-porous mold.

In addition to the amnion, additional dehydrated components can be added to the composition prior to and/or after micronization. In one aspect, other placental tissue components may be added. Placental tissue components can comprise intermediate tissue layer, chorion, or both, as well as dehydrated, micronized grafts of the same.

In one aspect, a dehydrated filler can be added. Examples of fillers include, but are not limited to, allograft pericardium, allograft acellular dermis, purified xenograft Type-1 collagen, biocellulose polymers or copolymers, biocompatible synthetic polymer or copolymer films, purified small intestinal submucosa, bladder acellular matrix, cadaveric fascia, bone particles (including cancellous and cortical bone particles), other polymers described above, or any combination thereof. A filler may be powdered, micronized, or in any other form such that the filler can be combined with the micronized placental component.

In another aspect, a dehydrated bioactive agent can be added to the composition prior to and/or after micronization.

Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells; concentrated amniotic fluid stem cells or stem cells grown in a bioreactor; or antibiotics. Upon application of the placental composition with bioactive agent to the region of interest, the bioactive agent is delivered to the region over time. Thus, the compositions described herein are useful as delivery devices of bioactive agents and other pharmaceutical agents when administered to a subject. Release profiles can be modified based on, among other things, the selection of the components used to make the composition as well as the size of the particles contained in the composition. Release profiles can further be modified by molding the composition as described above.

In some aspects, one or more stem cell recruiting factors that enhance stem cell chemotaxis and or recruitment may be added to a placental composition of the present technology. In other aspects, stem cell recruiting factors can be added to the micronized placental composition. Alternatively, stem cell recruiting factors may be added to layers of a laminate tissue graft prior to micronization. Thus, for example, cytokines, chemokines, growth factors, extracellular matrix components and other bioactive materials can be added to the modified amnion composition to enhance native stem cell recruitment. Specific non-limiting examples of stem cell recruiting factors may include one or more of the following: CC chemokines, CXC chemokines, C chemokines, or $CX_3C$ chemokines. Other stem cell recruiting factors may further include growth factors such as α-Fibroblast Growth Factor (αFGF or αFGF-1), β-Fibroblast Growth Factor (βFGF-1 or βFGF-2), Platelet-Derived Growth Factor (PDGF), Vascular Endothelial Growth Factor (VEGF-A, B, C, D or E), Angiopoietin-1 and -2, Insulin-like Growth Factor (IGF-1), Bone Morphogenic Protein (BMP-2 and -7), Transforming Growth Factor-α and -β (TGF-α and TGF-β), Epidermal Growth Factor (EGF), Connective Tissue Growth Factor (CTGF), Hepatocyte Growth Factor (HGF), Human Growth Hormone (HGH), Keratinocyte Growth Factor (KGF), Tumor Necrosis Factor-α (TNF-α), Leukemia Inhibitory Factor (LIF), Nerve Growth Factor (NGF), Stromal cell derived factor 1 (SDF-1α), Granulocyte Macrophage Colony Stimulating Factor (GM-CSF) and other factors as is known in the art.

Plasticizers

In yet another aspect, the placental composition is admixed with at least one plasticizer. One skilled in the art would select a suitable plasticizer based on the biocompatibility of the plasticizer, effect of plasticizer on the degradation or erosion rate of the placental tissue composition in vivo, and/or effect of the plasticizer on the strength, flexibility, consistency, hydrophobicity and/or hydrophilicity of the composition.

The terms "plasticizer" and "plasticizing agent" can be used interchangeably in the present invention. A plasticizing agent can include any agent or combination of agents that can be added to modify the mechanical properties of the composition or a product formed from the composition.

Without intending to be bound by any theory or mechanism of action, plasticizers can be added, for example, to reduce crystallinity, lower the glass-transition temperature (Tg), or reduce the intermolecular forces between components within the composition, with a design goal that may include creating or enhancing a flow between components in the composition. The mechanical properties that are modified include, but are not limited to, Young's modulus, tensile strength, impact strength, tear strength, and strain-to-failure. A plasticizer can be monomelic, polymeric, co-polymeric, or a combination thereof, and can be added to a composition with or without covalent bonding. Plasticization and solubility are analogous to the extent that selecting a plasticizer involves considerations similar to the considerations in selecting a solvent such as, for example, polarity. Furthermore, plasticizers can also be added to a composition through covalent bonding that changes the molecular structure of the composition through copolymerization.

Examples of plasticizing agents include, but are not limited to, low molecular weight polymers such as, for example, single-block polymers, multi-block polymers, and copolymers; oligomers such as, for example, lactic acid oligomers including, but not limited to, ethyl-terminated oligomers of lactic acid; dimers of cyclic lactic acid and glycolic acid; small organic molecules; hydrogen bond forming organic compounds with and without hydroxyl groups; polyols such as low molecular weight polyols having aliphatic hydroxyls; alkanols such as butanols, pentanols and hexanols; sugar alcohols and anhydrides of sugar alcohols; polyethers such as poly(alkylene glycols); esters such as citrates, phthalates, sebacates and adipates; polyesters; aliphatic acids; saturated and unsaturated fatty acids; fatty alcohols; cholesterol; steroids; phospholipids such as, for example, lecithin; proteins such as animal proteins and vegetable proteins; oils such as, for example, the vegetable oils and animal oils; silicones; acetylated monoglycerides; diglycerides; triglycerides; amides; acetamides; sulfoxides; sulfones; pyrrolidones; oxa acids; diglycolic acids; and any analogs, derivatives, copolymers and combinations thereof.

In some embodiments, the plasticizers include, but are not limited to other polyols such as, for example, caprolactone diol, caprolactone triol, sorbitol, erythritol, glucidol, mannitol, sorbitol, sucrose, and trimethylol propane. In other embodiments, the plasticizers include, but are not limited to, glycols such as, for example, ethylene glycol, diethylene glycol, Methylene glycol, tetraethylene glycol, propylene glycol, butylene glycol, 1,2-butylene glycol, 2,3-butylene glycol, styrene glycol, pentamethylene glycol, hexamethylene glycol; glycol-ethers such as, for example, monopropylene glycol monoisopropyl ether, propylene glycol monoethyl ether, ethylene glycol monoethyl ether, and diethylene glycol monoethyl ether; and any analogs, derivatives, copolymers and combinations thereof.

In other embodiments, the plasticizers include, but are not limited to esters such as glycol esters such as, for example, diethylene glycol dibenzoate, dipropylene glycol dibenzoate, methylene glycol caprate-caprylate; monostearates such as, for example, glycerol monostearate; citrate esters; organic acid esters; aromatic carboxylic esters; aliphatic dicarboxylic esters; fatty acid esters such as, for example, stearic, oleic, myristic, palmitic, and sebacic acid esters; triacetin; poly(esters) such as, for example, phthalate polyesters, adipate polyesters, glutate polyesters, phthalates such as, for example, dialkyl phthalates, dimethyl phthalate, diethyl phthalate, isopropyl phthalate, dibutyl phthalate, dihexyl phthalate, dioctyl phthalate, diisononyl phthalate, and diisodecyl phthalate; sebacates such as, for example, alkyl sebacates, dimethyl sebacate, dibutyl sebacate; hydroxyl-esters such as, for example, lactate, alkyl lactates, ethyl lactate, butyl lactate, allyl glycolate, ethyl glycolate, and glycerol monostearate; citrates such as, for example, alkyl acetyl citrates, triethyl acetyl citrate, tributyl acetyl citrate, trihexyl acetyl citrate, alkyl citrates, triethyl citrate, and tributyl citrate; esters of castor oil such as, for example, methyl ricinolate; aromatic carboxylic esters such as, for example, trimellitic esters, benzoic esters, and terephthalic esters; aliphatic dicarboxylic esters such as, for example, dialkyl adipates, alkyl allylether diester adipates, dibutoxyethoxyethyl adipate, diisobutyl adipate, sebacic esters, azelaic esters, citric esters, and tartaric esters; and fatty acid esters such as, for example, glycerol, mono- di- or triacetate, and sodium diethyl sulfosuccinate; and any analogs, derivatives, copolymers and combinations thereof.

In other embodiments, the plasticizers include, but are not limited to ethers and polyethers such as, for example, poly(alkylene glycols) such as poly(ethylene glycols) (PEG), polypropylene glycols), and poly(ethylene/propylene glycols); PEG derivatives such as, for example, methoxy poly(ethylene glycol) (mPEG); and ester-ethers such as, for example, diethylene glycol dibenzoate, dipropylene glycol dibenzoate, and triethylene glycol caprate-caprylate; and any analogs, derivatives, copolymers and combinations thereof.

In other embodiments, the plasticizers include, but are not limited to, amides such as, for example, oleic amide, erucic amide, and palmitic amide; alkyl acetamides such as, for example, dimethyl acetamide; sulfoxides such as for example, dimethyl sulfoxide; pyrrolidones such as, for example, n-methyl pyrrolidone; sulfones such as, for example, tetramethylene sulfone; acids such as, for example, oxa monoacids, oxa diacids such as 3,6,9-trioxaundecanedioic acid, polyoxa diacids, ethyl ester of acetylated citric acid, butyl ester of acetylated citric acid, capryl ester of acetylated citric acid, and diglycolic acids such as dimethylol propionic acid; and any analogs, derivatives, copolymers and combinations thereof.

In other embodiments, the plasticizers include, but are not limited to vegetable oils including, but not limited to, epoxidized soybean oil; linseed oil; castor oil; coconut oil; fractionated coconut oil; epoxidized tallates; and esters of fatty acids such as stearic, oleic, myristic, palmitic, and sebacic acid; essential oils including, but not limited to, angelica oil, anise oil, arnica oil, aurantii aetheroleum, valerian oil, basilici aetheroleum, bergamot oil, savory oil, bucco aetheroleum, camphor, cardamomi aetheroleum, cassia oil, chenopodium oil, chrysanthemum oil, cinae aetheroleum, citronella oil, lemon oil, citrus oil, costus oil, curcuma oil, carlina oil, elemi oil, tarragon oil, eucalyptus oil, fennel oil, pine needle oil, pine oil, filicis, aetheroleum, galbanum oil, gaultheriae aetheroleum, geranium oil, guaiac wood oil, hazelwort oil, iris oil, hypericum oil, calamus oil, chamomile oil, fir needle oil, garlic oil, coriander oil, carraway oil, lauri aetheroleum, lavender oil, lemon grass oil, lovage oil, bay oil, lupuli strobuli aetheroleum, mace oil, marjoram oil, mandarine oil, melissa oil, menthol, millefolii aetheroleum, mint oil, clary oil, nutmeg oil, spikenard oil, clove oil, neroli oil, niaouli, olibanum oil, ononidis aetheroleum, opopranax oil, orange oil, oregano oil, orthosiphon oil, patchouli oil, parsley oil, petit-grain oil, peppermint oil, tansy oil, rosewood oil, rose oil, rosemary oil, rue oil, sabinae aetheroleum, saffron oil, sage oil, sandalwood oil, sassafras oil, celery oil, mustard oil, serphylli aetheroleum, immortelle oil, fir oil, teatree oil, terpentine oil, thyme oil, juniper oil, frankincense oil, hyssop oil, cedar wood oil, cinnamon oil, and cypress oil; and other oils such as, for example, fish oil; and any analogs, derivatives, copolymers and combinations thereof.

It should be appreciated that, in some embodiments, one of skill in the art may select one or more particular plasticizing agents in order to exclude any one or any combination of the above-described plasticizing agents.

In some embodiments, the plasticizing agent can include a component that is water-soluble. In other embodiments, the plasticizing agent can be modified to be water-soluble. In some embodiments, the plasticizing agent can include a component that is lipid-soluble. In other embodiments, the plasticizing agent can be modified to be lipid-soluble. Any functional group can be added to modify the plasticizer's behavior in a solvent such as, for example, body fluids that are present in vivo.

In a further aspect, the in vivo degradation or erosion rate of the placental composition, as well as the density and cohesiveness of the components, can be modified, for example, by cross-linking. The components can be homologously cross-linked and/or heterologously crosslinked. For example, the amnion can be cross-linked with itself, the intermediate tissue layer, chorion, a second amnion tissue and/or a filler. For example, a cross-linking agent can be added to the composition (e.g., amnion, chorion, intermediate tissue layer, filler, or any combination thereof as individual components and/or as tissue grafts) prior to and/or after dehydration, micronization, and/or mixing. In general, the cross-linking agent is nontoxic and non-immunogenic.

As used herein, the term "homologously cross-linked" refers to cross-linking within one component of the amnion composition. For example, the amnion can be cross-linked with itself.

As used herein, the term "heterologously cross-linked" refers to cross-linking between different components of the placental composition. For example, the amnion can be cross-linked with the intermediate tissue layer, chorion, a second amnion tissue and/or a filler.

When the amnion, intermediate tissue layer, chorion (or a tissue graft thereof), and/or filler are treated with the cross-linking agent, the cross-linking agent can be the same or different. In one aspect, the amnion, intermediate tissue layer, chorion, and/or filler can be treated separately with a cross-linking agent or, in the alternative, the amnion, intermediate tissue layer, chorion, and/or filler can be treated together with the same cross-linking agent. In certain aspects, the amnion, intermediate tissue layer, chorion, and/or filler can be treated with two or more different cross-linking agents. The conditions for treating the amnion, intermediate tissue layer, chorion, and filler can vary. In other aspects, the amnion, intermediate tissue layer, chorion and/or filler can be treated with a cross-linking agent before or after micronization. In one aspect, the concentration of the cross-linking agent is from 0.1 M to 5 M, 0.1 M to 4 M, 0.1 M to 3 M, 0.1 M to 2 M, or 0.1 M to 1 M. Preferably, the components are cross-linked prior to dehydration such that the cross-linked components have a sufficiently low water content to permit compression or molding in a non-porous mold.

In certain aspects, the placental composition can be treated with the cross-linking agent. Preferably, one or more components of the placental composition are subjected to gas/fume cross-linking before or after micronization such that the water content of the component being cross-linked is maintained at a low level, e.g., less than about 20%, less than about 15%, less than about 10%, or less than about 5%. The cross-linking agent generally possesses two or more functional groups capable of reacting with proteins to produce covalent bonds. In one aspect, the cross-linking agent possesses groups that can react with amino groups present on the protein. Examples of such functional groups include, but are not limited to, hydroxyl groups, substituted or unsubstituted amino groups, carboxyl groups, and aldehyde groups. In one aspect, the cross-linker can be a dialdehyde such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N-[alpha-maleimidoacetoxy] succinimide ester, p-azidophenyl glyoxal monohydrate, bis-[beta-(4-azidosalicylamido)ethyl]disulfide, bis-[sulfosuccinimidyl]suberate, dithiobis[succinimidyl]propionate, disuccinimidyl suberate, and 1-ethyl-3-[3-dimethylaminopropyl]carbodiimide hydrochloride, a bifunctional oxirane (OXR), ethylene glycol diglycidyl ether (EGDE), nordihydroguaiaretic acid (NDGA).

In one aspect, sugar is the cross-linking agent, where the sugar can react with proteins present in the amnion, intermediate tissue layer, chorion, Wharton's jelly, and/or filler to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as a cross-linking agent include, but are not limited to, D-ribose, glycerone, altrose, talose, ertheose, glucose, lyxose, mannose, xylose, gulose, arabinose, idose, allose, galactose, maltose, lactose, sucrose, cellibiose, gentibiose, melibiose, turanose, trehalose, isomaltose, or any combination thereof.

In one aspect, the chelating agent is a cross linking agent. In one aspect, the chelating agent is substantially not involved in cross-linking of the component(s).

In yet another embodiment of the invention, the metal ion incorporated into the composition is bound to a quinone group and/or a catechol group present in the cross-linked placental composition. In other embodiments of the invention, the metal ion incorporated into the composition may be bound to a basic nitrogen atom, non-limiting examples of which include amino, or mono- or di-alkylated amino, and imidazole. In certain aspects, the metal ion is a platinum anticancer agent, such as platinum (+2) and/or platinum (+4). In certain preferred aspects, the platinum anticancer agent comprises a cis-diamino platinum moiety. As used herein the term "amino" refers to ammonia or a cycloalkyl amine, or a heteroaryl or a heterocyclyl amine, where the platinum coordinating nitrogen atom can be a part of the ring system or derivatize the ring system. Examples of cis-diamino platinum moieties and other platinum moieties useful in this invention are described, e.g., in Kostova, Recent Patents on Anti-Cancer Drug Discovery, 2006, 1, 1-22, which is incorporated herein in its entirety by reference. In other aspects, the platinum incorporated into the construct is present in an amount of between about 0.1% to about 30%.

In certain aspects, the placental composition provides a sustained release of metal ion, wherein the sustained release comprises a plurality of release rates including an immediate release, an intermediate release, an extended release or any combination of release rates thereof. In other aspects, the plurality of release rates are adjusted to provide a suitable range of release rates, wherein the range of release rates comprises from about 1 minute to about 60 days, or any range therein.

The placental compositions can be formulated variously depending on their mode of delivery and their delivery site. In some embodiments, the micronized placental composition, such as amnion or chorion compositions are compacted into a shape such as a pellet or an implant shaped as the graphite tube in a pencil. Unit lengths or doses of such shaped solid dosage forms are also provided. Such solid forms of the compositions can be administered topically to a site needing anticancer or other treatment, or may be administered into a patient by using dry, solid injection techniques well known and/or commercially available, or their obvious modifications. Non-limiting examples of such solid injections techniques include, the Glide SDI, solid injection system.

In other embodiments, the placental compositions are formulated as a viscous fluid. Such viscous formulations may preferably include non-aqueous organic liquids, which can include polymers such as polyethylene glycols, Polaxamer® polymers, and the like, and/or small molecule organic solvents. Such viscous formulations may be administered, preferably site specifically, using high pressure syringes that are well known and/or commercially available, or obvious modifications thereof. Non limiting examples of such high pressure syringes include those described in U.S. Pat. No. 6,503,244 (incorporated herein by reference) and the likes.

The present invention includes any combination of amnion, filler, plasticizer, and/or chelator, as would be understood by one of skill in the art. The amnion and/or filler optionally is cross linked. In one embodiment, the components are not cross linked. In an embodiment, the amnion and/or filler is homologously cross linked. In an embodiment, the amnion and/or filler is heterologously cross linked. The following tables provide non-limiting examples of potential embodiments of the invention. A person of skill in the art would understand such embodiments may further comprise other components or aspects as provided herein.

| Amnion | Chelator Location | Filler | Plasticizer |
|---|---|---|---|
| cross-linked | amnion | — | − |
| not cross-linked | amnion | — | − |
| cross-linked | amnion | cross-linked | − |
| not cross-linked | amnion | cross-linked | − |
| cross-linked | amnion | not cross-linked | − |
| not cross-linked | amnion | not cross-linked | − |
| cross-linked | amnion | — | + |
| not cross-linked | amnion | — | + |
| cross-linked | amnion | cross-linked | + |
| not cross-linked | amnion | cross-linked | + |
| cross-linked | amnion | not cross-linked | + |
| not cross-linked | amnion | not cross-linked | + |
| cross-linked | collagen | cross-linked | − |
| not cross-linked | collagen | cross-linked | − |
| cross-linked | collagen | not cross-linked | − |
| not cross-linked | collagen | not cross-linked | − |
| cross-linked | collagen | cross-linked | + |
| not cross-linked | collagen | cross-linked | + |
| cross-linked | collagen | not cross-linked | + |
| not cross-linked | collagen | not cross-linked | + |
| cross-linked | plasticizer | — | + |
| not cross-linked | plasticizer | — | + |
| cross-linked | plasticizer | cross-linked | + |
| not cross-linked | plasticizer | cross-linked | + |
| cross-linked | plasticizer | not cross-linked | + |
| not cross-linked | plasticizer | not cross-linked | + |
| cross-linked | amnion + collagen | cross-linked | − |
| not cross-linked | amnion + collagen | cross-linked | − |
| cross-linked | amnion + collagen | not cross-linked | − |
| not cross-linked | amnion + collagen | not cross-linked | − |
| cross-linked | amnion + collagen | — | + |
| not cross-linked | amnion + collagen | — | + |
| cross-linked | amnion + collagen | cross-linked | + |
| not cross-linked | amnion + collagen | cross-linked | + |
| cross-linked | amnion + collagen | not cross-linked | + |
| not cross-linked | amnion + collagen | not cross-linked | + |
| cross-linked | amnion + plasticizer | — | + |
| not cross-linked | amnion + plasticizer | — | + |

-continued

| Amnion | Chelator Location | Filler | Plasticizer |
|---|---|---|---|
| cross-linked | amnion + plasticizer | cross-linked | + |
| not cross-linked | amnion + plasticizer | cross-linked | + |
| cross-linked | amnion + plasticizer | not cross-linked | + |
| not cross-linked | amnion + plasticizer | not cross-linked | + |
| cross-linked | amnion + collagen + plasticizer | cross-linked | + |
| not cross-linked | amnion + collagen + plasticizer | cross-linked | + |
| cross-linked | amnion + collagen + plasticizer | not cross-linked | + |
| not cross-linked | amnion + collagen + plasticizer | not cross-linked | + |
| cross-linked | chorion | — | − |
| not cross-linked | chorion | — | − |
| cross-linked | chorion | cross-linked | − |
| not cross-linked | chorion | cross-linked | − |
| cross-linked | chorion | not cross-linked | − |
| not cross-linked | chorion | not cross-linked | − |
| cross-linked | chorion | — | + |
| not cross-linked | chorion | — | + |
| cross-linked | chorion | cross-linked | + |
| not cross-linked | chorion | cross-linked | + |
| cross-linked | chorion | not cross-linked | + |
| not cross-linked | chorion | not cross-linked | + |
| cross-linked | collagen | cross-linked | − |
| not cross-linked | collagen | cross-linked | − |
| cross-linked | collagen | not cross-linked | − |
| not cross-linked | collagen | not cross-linked | − |
| cross-linked | collagen | cross-linked | + |
| not cross-linked | collagen | cross-linked | + |
| cross-linked | collagen | not cross-linked | + |
| not cross-linked | collagen | not cross-linked | + |
| cross-linked | plasticizer | — | + |
| not cross-linked | plasticizer | — | + |
| cross-linked | plasticizer | cross-linked | + |
| not cross-linked | plasticizer | cross-linked | + |
| cross-linked | plasticizer | not cross-linked | + |
| not cross-linked | plasticizer | not cross-linked | + |
| cross-linked | chorion + collagen | cross-linked | − |
| not cross-linked | chorion + collagen | cross-linked | − |
| cross-linked | chorion + collagen | not cross-linked | − |
| not cross-linked | chorion + collagen | not cross-linked | − |
| cross-linked | chorion + collagen | — | + |
| not cross-linked | chorion + collagen | — | + |
| cross-linked | chorion + collagen | cross-linked | + |
| not cross-linked | chorion + collagen | cross-linked | + |
| cross-linked | chorion + collagen | not cross-linked | + |
| not cross-linked | chorion + collagen | not cross-linked | + |
| cross-linked | chorion + plasticizer | — | + |
| not cross-linked | chorion + plasticizer | — | + |
| cross-linked | chorion + plasticizer | cross-linked | + |
| not cross-linked | chorion + plasticizer | cross-linked | + |
| cross-linked | chorion + plasticizer | not cross-linked | + |
| not cross-linked | chorion + plasticizer | not cross-linked | + |
| cross-linked | chorion + collagen + plasticizer | cross-linked | + |
| not cross-linked | chorion + collagen + plasticizer | cross-linked | + |
| cross-linked | chorion + collagen + plasticizer | not cross-linked | + |
| not cross-linked | chorion + collagen + plasticizer | not cross-linked | + |

Another embodiment of the invention is directed to a method of manufacturing a placental composition, such as amnion or chorion composition comprising: providing an placental layer or placental tissue graft; dehydrating the placental layer or graft; micronizing the placental layer or graft; and binding one or more chelating agents to the placental layer or graft, wherein the binding step may be before the dehydrating step or before or after the micronizing step.

Another embodiment of the invention is directed to a method of manufacturing a placental composition, such as amnion or chorion composition comprising: providing a placental layer or placental tissue graft; dehydrating the placental layer or graft; micronizing the placental layer or graft; binding one or more chelating agents to the placental layer or graft, wherein the binding step may be before the dehydrating step or before or after the micronizing step; and chelating a pharmacologically active metal ion to the composition, wherein the chelating step can be performed at any time after the binding step.

Another embodiment of the invention is directed to a method of manufacturing a placental composition, such as amnion or chorion composition comprising: providing a placental layer or placental tissue graft and a filler; dehydrating the placental layer or graft and optionally the filler; micronizing the placental layer or graft; and binding one or more chelating agents to the placental layer or graft and/or to the filler, wherein the binding step may be before the dehydrating step or before or after the micronizing step; and combining the layer or graft and the filler, wherein the combination step may be performed at any time during the process.

Another embodiment of the invention is directed to a method of manufacturing a placental composition, such as amnion or chorion composition comprising: providing a placental layer or placental tissue graft and a filler; dehydrating the placental layer or graft and optionally the filler; micronizing the placental layer or graft; binding one or more chelating agents to the placental layer or graft and/or to the filler, wherein the binding step may be before the dehydrating step or before or after the micronizing step; combining the layer or graft and the filler, wherein the combination step may be performed at any time during the process; and chelating a pharmacologically active metal ion to the composition, wherein the chelating step can be performed at any time after the binding step.

The pharmaceutical compositions described herein can be administered in a number of ways depending on whether local or systemic treatment is desired, and on the area to be treated. In one aspect, administration can be by injection. In other aspects, the composition can be formulated to be applied internally to a subject. In other aspects, the composition can be applied topically, subdermally or subcutaneously.

III. Applications of Compositions Comprising Micronized Placental and/or Filler with One or More Chelating Agents Bound Thereto Therapeutic Applications The compositions comprising micronized placental compositions and/or filler with one or more chelating agents bound thereto described herein have numerous therapeutic applications.

In one aspect, provided herein is a method of treating a subject suffering from cancer amenable to treatment with platinum alkylators, the method comprising administering placental composition in the subject, wherein the composition comprises (a) micronized placental and one or more chelating moieties and (b) platinum chelated to the chelating moieties, to administer an effective amount of platinum into the subject. The placental composition optionally comprises a filler. The chelating moieties may be bound to the amnion, filler, or both.

In yet another embodiment, the invention is directed to a method of treating a subject in need of treatment for a cancer treatable with a metal-containing anticancer agent, comprising: a) implanting a medical construct in a subject, wherein the medical construct comprises a micronized placental composition and an anticancer amount of an anticancer agent incorporated therein to provide a therapeutically effective amount of anticancer platinum in the construct, and b) releasing the anticancer agent from the composition, thereby inhibiting cancer. In one embodiment, the effective amount of anticancer agent, e.g. platinum, is released from the composition at a plurality of in vivo release rates. Methods of determining the therapeutically effective amount and/or appropriate mode of administration of the compounds and compositions provided herein will be apparent to the skilled artisan upon reading this disclosure and based on other methods known to them. In one embodiment, the placental composition optionally comprises a filler.

The present invention finds use in medical applications and animal studies. The term "medical" includes both human and veterinary uses. Suitable subjects of the present invention include, but are not limited to avians and mammals.

In particular embodiments, the subject is "in need of" the methods of the present invention, e.g., the subject may benefit from a surgical procedure implanting a composition of the present invention, such as a prosthesis or other device. In certain embodiments, after implantation, the compositions of the present invention can confer a therapeutic and/or prophylactic effect to the subject, such as prevent a disease and/or clinical symptom, reduce the severity of a disease and/or clinical symptom relative to what would occur in the absence of the methods of the prevent invention, and/or delay the onset and/or progression of a disease and/or clinical symptom. The methods of the present invention can provide complete and/or partial treatment and/or protection. In particular embodiments, after implantation in or administration to a subject, the compositions of the present invention treat and/or inhibit and/or protect against cancer, preferably those cancers that are treatable with platinum anticancer agents, in the subject.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Preparation of Micronized Composition

Amnion/chorion tissue grafts used here to produce the micronized particles were produced by the process described in US 2008/0046095, which is incorporated by reference in its entirety. Tissue grafts (4 cm×3 cm) and two 9.5 mm steel grinding balls were placed in 50 mL vials and the vials subsequently sealed. The vials were placed in the Cryo-block, and the Cryo-block was placed in a Cryo-rack. The Cryo-rack was placed into a liquid nitrogen holding Dewar. Tissue samples were subjected to vapor phase cooling for no more than 30-60 minutes. The Cryo-rack was removed from the Dewar, and the Cryo-block was removed from the Cryo-rack. The Cryo-block was placed into the Grinder (SPEX Sample Prep GenoGrinder 2010) and set at 1,500 rpm for 20 minutes. After 20 minutes has elapsed, the tissue is inspected to ensure micronization. If necessary, the tissue can be placed back into the Dewar for an additional 30-60 minutes, and moved to the grinder for an additional 20 minutes to ensure sufficient micronization. Once the tissue is sufficiently micronized it is sorted using a series of American Standard ASTM sieves. The sieves were placed in the following order: 355 µm, 300 µm, 250 µm, 150 µm, and 125 nm. The micronized material was transferred from the 50 mL vials to the 355 µm sieve. Each sieve was agitated individually in order to thoroughly separate the micronized particles. Once the micronized particles have been effectively separated using the sieves, the micronized particles having particle sizes of 355 µm, 300 µm, 250 µm, 150 µm, and 125 µm were collected in separate vials.

Example 2

Preparation of Tissue Grafts with Micronized Placental Tissue

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

A detailed description of reinforced placental tissue grafts is provided in U.S. Patent Application Publication No. 2014/0067058 which application is incorporated herein by reference in its entirety.

A detailed description of making and using micronized placental tissue and extracts thereof is provided in U.S. Patent Application Publication No. 2014/0050788 which application is incorporated herein by reference in its entirety.

Example 3

Cell Migration in the Presence of EpiFix®

Human mesenchymal stem cells (human MSC) were evaluated in cell culture in the presence of samples of EpiFix® to determine whether the EpiFix® would induce migration of the human MSC. EpiFix® is a layer of amnion and chorion with the epithelial layer intact.

Materials and Methods

Figure 4:
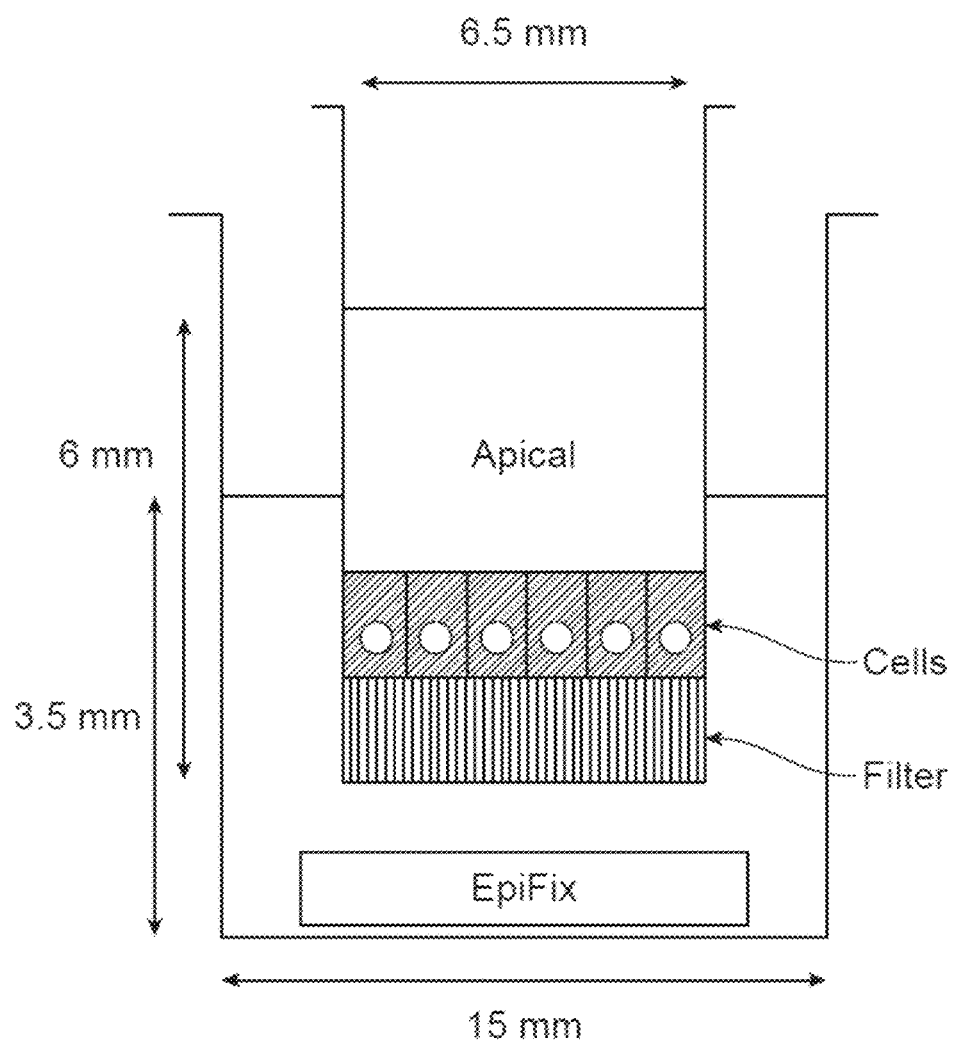
FIG. 4 shows a schematic for a cell culture insert for stem cell migration assays described in Example 3.

Standard migration assays were performed in 24-well cell culture inserts with 8-µm pore membrane filters at the bottom of the insert (see FIG. 4; BD Biosciences). 24 hours prior to the start of the experiment, human MSCs (one donor, passage 3) were cultured in serum free media, and 300 µL of 5 µg/mL fibronectin in PBS was placed into each cell culture insert to enable adsorption of fibronectin to the cell culture insert surface overnight.

On the day of the experiment, 700 µL of serum-free culture medium was loaded into the bottom wells of the plate, followed by the addition of differently sized portions of sterilized EpiFix® (Low: 1.5-mm diameter disk; Medium: 4-mm diameter disk; High: 12×13 mm square, trimmed into 3-4 mm square pieces; n=6 EpiFix® tissue donors tested). One square centimeter of EpiFix® weighs 4 mg. Serum-free medium and medium with 10% fetal bovine serum (n=6) acted as negative and positive controls, respectively. Human MSCs (40,000 cells in 300 μL) were then loaded into the cell culture inserts and cultured for 24 hours. Then, both sides of the cell culture inserts were rinsed with PBS, and non-migrating cells in the upper portion insert were removed with a cotton-tipped applicator. Cells on the lower side of the insert plus the membrane filter were fixed in 10% formalin for 20 minutes, then rinsed and stained with hematoxylin for 5 min. The number of cells migrating through the membrane were counted on the lower surface of the membrane with an inverted microscope (Nikon TE2000; SPOT Software 4.6).

Data were normalized to the 10% FBS positive control and are expressed as mean±standard deviation of counted, migrated cells per 100× field micrograph for each sample well. Statistical comparisons were performed using a Box-Cox transformation to normalize data variance, followed by one-factor analysis of variance (ANOVA) with Tukey's honestly significant difference post-hoc test.

Results

Figure 5:
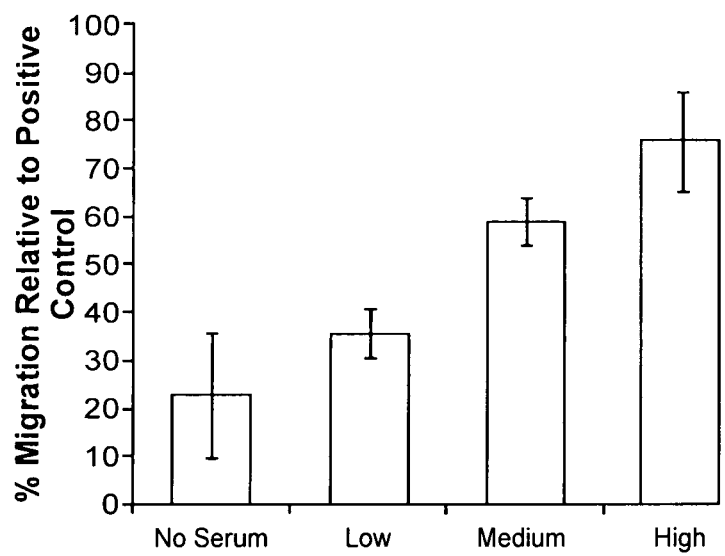
FIG. 5 shows a bar graph of percent cell migration in human mesenchymal stem cells (MSCs) cultured in the presence of various amounts of EpiFix®. Details are described in Example 3.

The Low group (1.5 mm diameter disk) containing the smallest EpiFix® sample was not significantly different from the no serum negative control (see bar graph in FIG. 5). Both the Medium group (4 mm diameter disk) and the High group (12×13 mm square, trimmed into 3-4 mm square pieces) were statistically higher than the no serum control (about 60% and 75% migration relative to control; see FIG. 5), indicating that EpiFix® stimulated cell migration. The High group was not significantly different from the Medium group. The results indicate that the EpiFix® product contains one or more factors that attract human mesenchymal stem cells.

Example 4

Stem Cell Recruitment in Mice Receiving EpiFix® Implants

A study was undertaken to determine whether EpiFix® implanted in normal mice causes recruitment of stem/progenitor cells, focusing on mouse hematopoietic stem cells (HSCs) and mouse mesenchymal stem cells (mouse MSCs).

Materials and Methods

EpiFix® products from six donors were used for implantation in normal mice. A 5×5 mm square of EpiFix® was surgically placed subcutaneously in 4 month old FVB/NJ mice (weighing between about 23.50 g and about 30 g). Four mice were implanted per sample per time point. The time points were 3, 7, 14 and 28 days. The negative controls were normal skin and sham operated mice (surgical incision but no implant). Decellularized dermal matrix (acellular dermal matrix; ADM) was used as the comparative implant (Type I collagen, no cytokines). The implant and overlying skin was harvested for fluorescence-activated cell sorting (FACS).

Implants and overlying skin were harvested, cut into 1 mm² sections, and incubated in a 0.15% dispase/0.075% collagenase solution at 37° C. for 1 hour. After centrifugation, samples were stained with a lineage antibody cocktail as described below. CD31 antibody was added followed by Alexa Fluor 647 anti-rat secondary antibody. Phycoerythrin-Cy7-conjugated anti-CD45 antibody was incubated last. Samples were prepared and analyzed as described below.

Samples were incubated with a lineage negative (lin⁻) antibody cocktail (Ter119/CD4/CD8a/Gr-1/CD45R/CD11b) followed by phycoerythrin-Cy5 anti-rat secondary antibody. For mesenchymal stem cell analysis, conjugated antibodies were added against CD45 (phycoerythrin-Cy7) and Sca-1 (fluorescein isothiocyanate). For hematopoietic stem cell analysis, conjugated antibodies were added against CD45 (phycoerythrin-Cy7), c-Kit (phycoerythrin), and Sca-1 (fluorescein isothiocyanate). Samples were incubated with antibodies for 30 minutes and then washed by adding 5 volumes of 2% fetal bovine serum in phosphate-buffered saline with 2 mM ethylenediaminetetraacetic acid. Cells were centrifuged and then re-suspended in propidium iodide for 1 minute at 4° C. Samples were analyzed using an LSR Flow Cytometer. Using CellQuest software), samples were gated for lin⁻/Sca-1⁺/CD45⁻ to define mesenchymal stem cells and for lin⁻/Sca-1⁺/c-Kit⁺/CD45⁺ to define hematopoietic stem cells.

Results

Figure 6A:
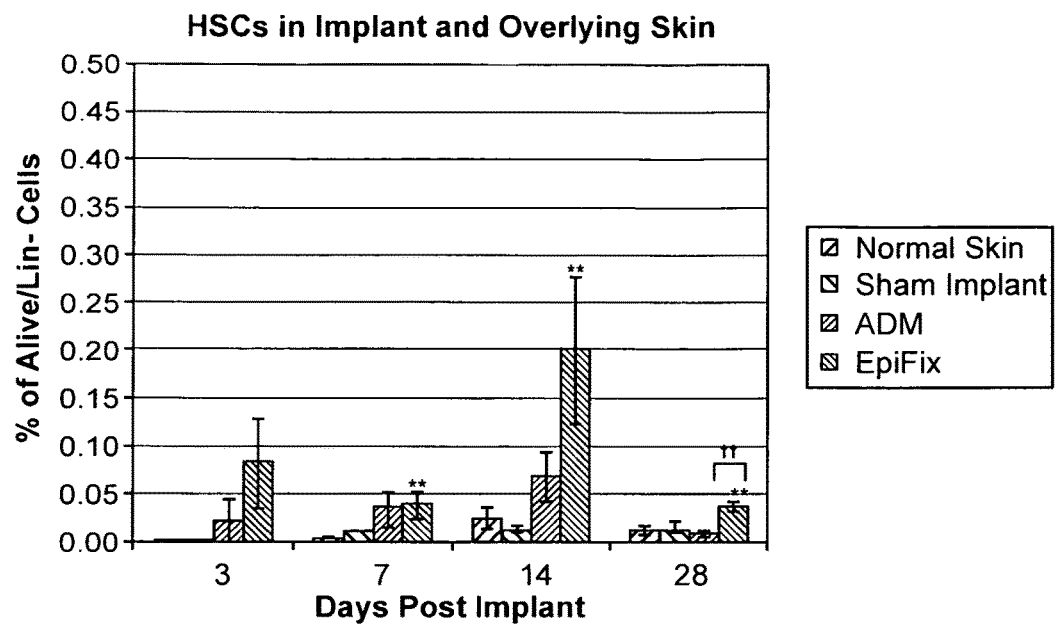
FIG. 6A shows a bar graph of percentage living/Lin$^-$ mouse hematopoietic stem cells in normal skin, sham implant, acellular dermal matrix, and EpiFix® at 3, 7, 14, and 28 days post implant. Values shown are means+/−standard deviation, n=4 specimens.  indicates p<0.05 when comparing EpiFix® or control ADM to normal skin and sham implant via one-way ANOVA. †† indicates p<0.05 when comparing EpiFix® to control ADM via two tailed t-test.

Mouse HSCs were significantly increased following EpiFix® implantation compared to negative controls at days 7, 14 and 28 (see FIG. 6A). Mouse HSCs remained significantly increased in the EpiFix® samples at day 28 compared to ADM.

Figure 6B:
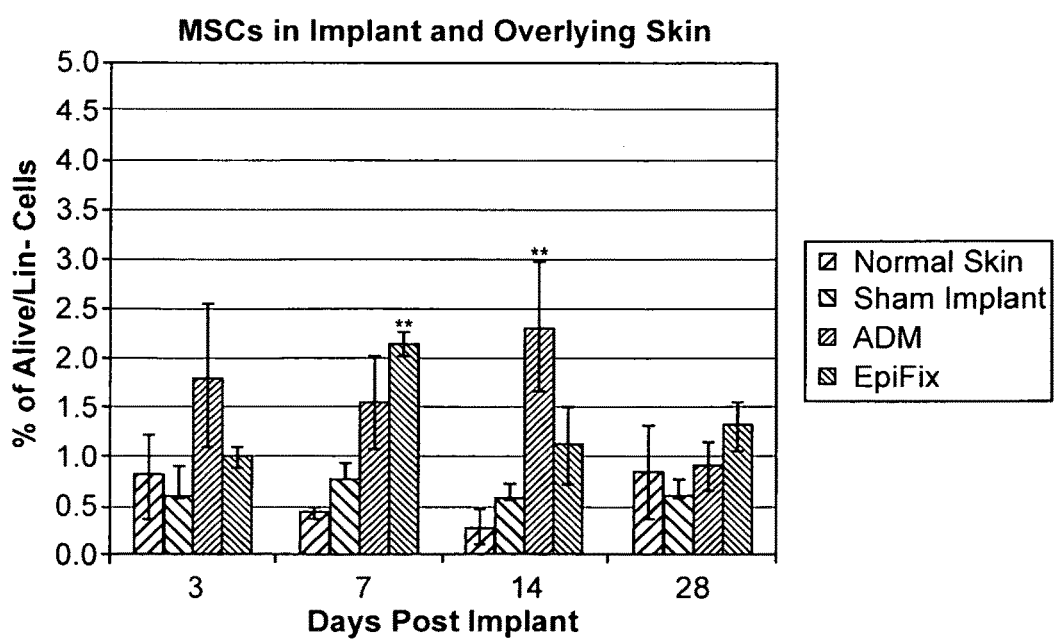
FIG. 6B shows a bar graph of percentage living/Lin$^-$ mouse mesenchymal cells in normal skin, sham implant, acellular dermal matrix, and EpiFix® at 3, 7, 14, and 28 days post implant. Values shown are means+/−standard deviations, n=4 specimens.  indicates p<0.05 when comparing EpiFix® or control ADM to normal skin and sham implant via one-way ANOVA. Details are described in Example 4.

Mouse MSCs were significantly increased following EpiFix® implantation compared to negative controls at day 7 (see FIG. 6B). The average percentages of mouse MSCs were increased at all time points compared to negative controls.

Thus the data described above show that EpiFix® implants effectively recruit both HSCs and MSCs in vivo in normal mice. The data also show that EpiFix® leads to longer term HSC recruitment than acellular dermal matrix (ADM), supporting the hypothesis of a cytokine mediated effect of EpiFix®.

Example 5

Stem Cell Characterization in Mice Receiving EpiFix® Implants

A study was undertaken to characterize stem cells recruited to EpiFix® implantation sites in mice, using flow cytometry and immunohistochemistry.

Materials and Methods

Sterile, Purion® processed EpiFix® in a 5×5 mm square patch was implanted subcutaneously through a skin incision on the backs of sixteen 4 month old FVB/NJ mice. Identical skin incisions were made in another sixteen mice to function as a control treatment (sham). For comparison with a collagen scaffold, a 5×5 mm square patch of decellularized human dermis (acellular dermal matrix; ADM) was implanted subcutaneously on the backs of sixteen mice. Un-operated mice were used as a source of "normal" back skin for the analyses.

The surgical site was removed at 3, 7, 14 and 28 days following implantation for analyses of stem cells. Four animals/group were used at each time point. Stem cells were identified with two distinct methods: Fluorescence-activated cell sorting (FACS) and immunohistochemistry (IHC). For the FACS analysis, all cells were isolated from the amnion and associated regenerated tissue. The cells were fluorescently labeled with antibodies to specific stem cell markers. The identity and number of each cell type were determined with a flow cytometer.

Figure 7A:
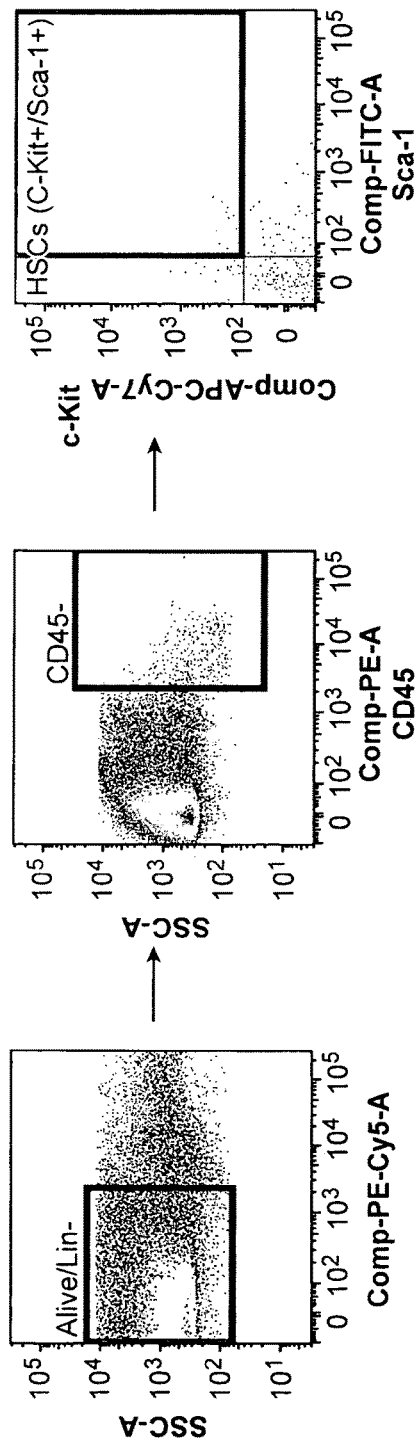
FIG. 7A shows representative FACS dot plots of cells detected using flow cytometry and fluorescent detection of CD45 and Sca-1.

For the immunohistochemical analyses, the membrane and associated regenerated tissue was fixed, sectioned for slides, and stained with specific antibodies to stem cells. Two antibodies were used for the immunohistochemistry:

anti-CD34, which specifically detects hematopoietic progenitor cells (HPC), and reacts with dermal progenitor cells, endothelial cells, dendritic cells; and anti-CD31, which detects endothelial cells. The stained tissue sections were examined microscopically and the presence and number of specific stem cell types were measured. For the experimental analysis, the relative number of each cell type was counted. The results were calculated as the percentage of each cell type (no. of immunostained cells/total number of cells). Two areas were analyzed immunohistochemically for cell recruitment: the tissue surrounding the implant and the implant itself Results Representative data from the FACS analyses are shown in FIG. 7A. The left panel shows the total number of cells in the sample. The middle panel shows the number of CD45 positive cells (in inset box). The right panel shows the number of Sca-1 positive cells (in inset box). CD45 and Sca-1 are specific markers for hematopoietic stem cells.

Figure 7B:
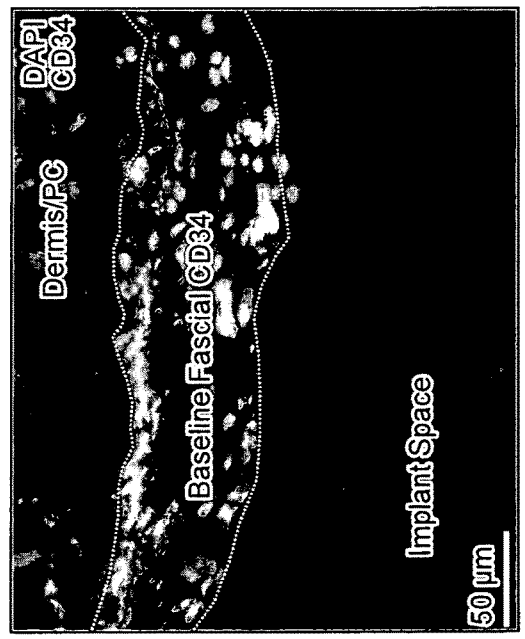
FIG. 7B shows photomicrograph of dermal tissue stained with DAPI which stains cell bodies, and CD34, which is a marker for hematopoietic stem cells. Details are described in Example 5.

FIG. 7B shows an exemplary immunohistochemistry image. The gray bar in the lower left corner represents 50 µm. The section was stained with DAPI (blue—stains all cells) and anti-CD34 (red). The place where the tissue is implanted in the experimental mice is shown for reference.

Hematopoietic progenitor cell (HPC) levels were significantly elevated in tissue surrounding EpiFix® implants at days 14 and 28 compared to negative controls. Hematopoietic progenitor cells were significantly increased in the tissue surrounding the EpiFix® implant at days 14 and 28 compared to collagen scaffold ADM control.

Progenitor cells were recruited into the EpiFix® implant. Intra-implant hematopoietic progenitor cells peaked at day 14 in the EpiFix® implant, and remained elevated at day 28. Average intra-implant hematopoietic progenitor cells were increased in the EpiFix® implant at days 14 and 28 compared to control ADM. Progenitor cells were not recruited into the ADM control implant.

Vascularization of the EpiFix® implant steadily increased from day 14 to day 28. The amount of new vessel formation in the EpiFix® implant was significantly greater than that in the ADM control on day 28.

These data establish that EpiFix® contains one or more factors that recruit both hematopoietic stem cells and mesenchymal stem cells to the site of injury. More of these stem cells were found in the EpiFix® membrane and associated regenerated tissue than in the sham or, more importantly, the control collagen scaffold. EpiFix® was significantly more effective than the control decellularized collagen scaffold in recruiting progenitor cells to colonize the implant site. There were more progenitor cells in the EpiFix® membrane than in the control collagen scaffold.

EpiFix® also induced new blood vessel formation in the associated regenerated tissue and the EpiFix® membrane itself. Vascularization in the EpiFix® membrane was significantly higher than in the collagen scaffold control.

Example 6

Preparation of Non-Cross-Linked Tissue-Chelator Conjugates

Various placental tissue grafts described above can be combined with at least 30 equivalents of dopamine under conventional amide forming conditions to provide for a plurality of chelating moieties bound to the placental tissue. The nitrogen of the dopamine reacts with a number of carboxylic acid groups of the amniotic collagen to form a carbodiamide linkage.

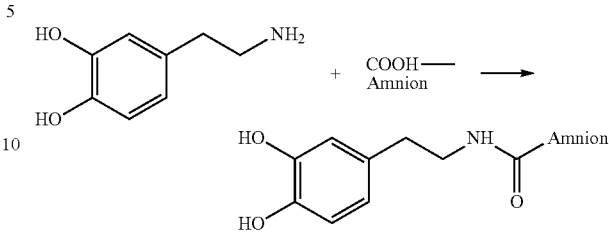

Example 7

Chelation of the Biologically Active Metal Ion with the Polymer Chelator Conjugate Dry non-cross-linked tissue-chelator conjugates described above are incubated in 1% (w/v) cis-diamino Pt(II) diaqua salt in water at room temperature for 16 hours. The grafts are then washed with deionized water and dried. Platinum content in the conjugates is measured e.g., by Inductively Coupled Plasma-Mass Spectrometry (ICP-MS). Results are expressed as µg/g, which is equivalent to parts per million (ppm).

The incorporation of platinum in the conjugates can produce a biomaterial imbibed with anticancer capabilities. As such, the method of incorporating platinum into tissue materials can provide a drug delivery device, preferably for anticancer drug delivery.

In some embodiments, the tissues utilized in the conjugates of the present invention also incorporate one or more stem cell recruiting factors that enhance stem cell chemotaxis and/or recruitment. Such compositions for recruiting stem cells are described in U.S. Patent Application Publication No. 2014/0106447, which application is incorporated herein by reference in its entirety. These stem cell recruiting factors in combination with the biologically active metal are abhorrent to aberrant stem cells, such as cancerous cells, and work against tumor-related recurrence of cancer.

It is evident from the above examples that the EpiFix® amniotic membrane allograft has the capability to attract or increase the flux of stem cells to the amnion. Thus, the amniotic membrane is a biologically derived polymer which attracts stem cells. Further, if the amniotic membrane is conjugated to the chelator moiety and a metal such as e.g., cisplatin, then the polymer conjugate can be used to kill stem cells, particularly aberrant stem cells such as tumor cells.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

A detailed description of suitable cross-linking agents and procedures is provided in U.S. Patent Application Publication No. 2014/0052247 which application is incorporated herein by reference in its entirety.

A detailed description of micronized placental tissue is provided in U.S. Patent Application Publication Nos. 2014/0052274 and 2014/0050788, which applications are incorporated herein by reference in their entireties.

A detailed description of cross-linked polymers comprising metal ions is provided in U.S. Patent Application Publication Nos. 2014/0141096, 2014/0142041, and U.S. patent application Ser. No. 13/860,473, all of which applications are incorporated herein by reference in their entireties.

What is claimed:

1. A composition comprising
   i) a micronized placental tissue component;
   ii) one or more chelating moieties; and
   iii) optionally, a biologically compatible filler;
   wherein the one or more chelating moieties are covalently bound to the placental tissue component and/or the filler, when the filler is present; and
   wherein a therapeutically effective amount of a pharmacologically active metal ion is chelated to the one or more chelating moieties.

2. The composition of claim 1, wherein the placental tissue component and/or filler is homologously cross-linked.

3. The composition of claim 1, wherein the placental tissue component and/or filler is heterologously cross-linked.

4. The composition of claim 1, wherein the filler is present in said composition and is a biologically compatible polymer.

5. The composition of claim 4, wherein the biologically compatible polymer is selected from the group consisting of collagen, hyaluronic acid, and a plasticizer.

6. The composition of claim 1, wherein the ratio of micronized placental tissue component to filler is between 1:99 and 99:1.

7. The composition of claim 1, wherein one or more of the chelating moieties cross-link the placental tissue component and/or the filler.

8. The composition of claim 1, wherein the one or more chelating moieties do not cross-link the placental tissue component.

9. The composition of claim 1, further comprising a pharmaceutically acceptable excipient.

10. The composition of claim 1, wherein the pharmacologically active metal ion is in an anticancer agent.

11. The composition of claim 10, wherein the anticancer agent comprises a platinum ion.

12. The composition of claim 11, wherein the anticancer agent is cisplatin.

13. The composition of claim 1, wherein the composition provides a sustained release of the metal ion.

14. The composition of claim 1, wherein the composition is molded.

15. The composition of claim 1, wherein the micronized placental tissue component is micronized amnion.

16. The composition of claim 15, further comprising micronized chorion, Wharton's jelly, and/or micronized intermediate tissue layer.

17. The composition of claim 1, wherein the micronized placental tissue component is micronized chorion.

18. A composition comprising
    i) micronized amnion;
    ii) a biologically compatible filler;
    iii) a biologically compatible plasticizer; and
    iv) one or more chelating moieties;
    wherein the one or more chelating moieties are covalently bound to the micronized amnion and/or the filler; and
    wherein a therapeutically effective amount of a pharmacologically active metal ion is chelated to the one or more chelating moieties.

19. The composition of claim 1, wherein the filler comprises bone particles.

* * * * *